(12) United States Patent
Starr

(10) Patent No.: US 11,839,480 B2
(45) Date of Patent: Dec. 12, 2023

(54) COMPUTER IMPLEMENTED METHOD FOR ANALYZING ELECTROENCEPHALOGRAM SIGNALS

(71) Applicant: MYNEURVA HOLDINGS, INC., Sheridan, WY (US)

(72) Inventor: Frederick Scott Starr, Puntarenas (CR)

(73) Assignee: MYNEURVA HOLDINGS, INC., Sheridan, WY (US)

( * ) Notice: Subject to any disclaimer, the term of this patent is extended or adjusted under 35 U.S.C. 154(b) by 146 days.

(21) Appl. No.: 17/121,987

(22) Filed: Dec. 15, 2020

(65) Prior Publication Data

US 2021/0290137 A1 Sep. 23, 2021

Related U.S. Application Data

(62) Division of application No. 15/685,985, filed on Aug. 24, 2017, now Pat. No. 10,863,912.

(51) Int. Cl.
*A61B 5/00* (2006.01)
*A61B 5/369* (2021.01)
(Continued)

(52) U.S. Cl.
CPC .............. *A61B 5/316* (2021.01); *A61B 5/369* (2021.01); *A61B 5/7275* (2013.01); *G16H 40/63* (2018.01);
(Continued)

(58) Field of Classification Search
None
See application file for complete search history.

(56) References Cited

U.S. PATENT DOCUMENTS 5,542,429 A * 8/1996 Feng ........................ A61B 5/30
600/515
6,658,287 B1 12/2003 Litt et al.
(Continued)

FOREIGN PATENT DOCUMENTS

EP 1 923 806 A1 5/2008
WO 2015/153958 A1 10/2015
(Continued)

OTHER PUBLICATIONS

Univeisity of Teshrskology Sydney (UTS); Non-Imiasive Prediction of Adverse Neural Events Using Brain Wave Activity; Sep. 14, 2015.
(Continued)

*Primary Examiner* — Etsub D Berhanu
(74) *Attorney, Agent, or Firm* — POLSINELLI PC

(57) ABSTRACT

A computer implemented method for analyzing electroencephalogram signals can include a plurality of sensors configured to contact a skull and capture the electroencephalogram signals, one or more computer memory units for storing computer instructions and data, and one or more processors configured to perform the operations of clustering the electroencephalogram signals using at least stored objective data and added subjective data including patient profile data to provide clustered data results and predicting one or more among a medical diagnosis, assessment, plan, necessary forms, or recommendations for follow up based on the clustered data results.

5 Claims, 20 Drawing Sheets

(51) Int. Cl.
  *A61B 5/316* (2021.01)
  *G16H 50/70* (2018.01)
  *G16H 40/63* (2018.01)
  *A61B 5/16* (2006.01)
  *G16H 50/20* (2018.01)
  *G16H 10/60* (2018.01)
  *G06F 16/22* (2019.01)

(52) U.S. Cl.
  CPC ............... *G16H 50/70* (2018.01); *A61B 5/16* (2013.01); *A61B 5/6814* (2013.01); *A61B 5/726* (2013.01); *A61B 5/7257* (2013.01); *A61B 2562/046* (2013.01); *G06F 16/22* (2019.01); *G16H 10/60* (2018.01); *G16H 50/20* (2018.01)

(56) References Cited

U.S. PATENT DOCUMENTS

| | | |
|---|---|---|
| 7,177,675 B2 | 2/2007 | Suffin et al. |
| 7,647,098 B2 | 1/2010 | Prichep |
| 7,884,069 B2 | 2/2011 | Schaebitz et al. |
| 8,239,142 B2 | 8/2012 | Collette et al. |
| 8,577,451 B2 | 11/2013 | Causevic |
| 9,053,222 B2 | 6/2015 | Lynn et al. |
| 9,451,303 B2 | 9/2016 | Kothuri et al. |
| 9,532,748 B2 | 1/2017 | Denison et al. |
| 9,706,939 B2 | 7/2017 | Collura et al. |
| 2002/0188216 A1 | 12/2002 | Kayyali et al. |
| 2004/0122709 A1 | 6/2004 | Avinash et al. |
| 2004/0127803 A1 | 7/2004 | Berkes et al. |
| 2008/0208073 A1 | 8/2008 | Causevic |
| 2011/0301486 A1 | 12/2011 | Van Hek et al. |
| 2013/0024213 A1 | 1/2013 | Poon |
| 2013/0090542 A1 | 4/2013 | Kipke et al. |
| 2014/0046696 A1 | 2/2014 | Higgins et al. |
| 2014/0051044 A1 | 2/2014 | Badower et al. |
| 2014/0194720 A1 | 7/2014 | Hua |
| 2014/0289172 A1 | 9/2014 | Rothman et al. |
| 2015/0088024 A1 | 3/2015 | Sackellares et al. |
| 2015/0157235 A1 | 6/2015 | Jelen et al. |
| 2015/0227702 A1 | 8/2015 | Krishna et al. |
| 2016/0132654 A1 | 5/2016 | Rothman et al. |
| 2016/0166169 A1 | 6/2016 | Badower et al. |
| 2016/0324435 A1 | 11/2016 | Kuzum et al. |
| 2017/0027466 A1 | 2/2017 | Kerth et al. |

FOREIGN PATENT DOCUMENTS

| | | |
|---|---|---|
| WO | 2016156171 A1 | 10/2016 |
| WO | 2016162820 A1 | 10/2016 |
| WO | 2016110804 A1 | 7/2017 |

OTHER PUBLICATIONS

Steven Warner, PhD,: Cheat Sheet for Neurcifeedback; Miami,. Forida; jam 2013; 28 pages.

Mi-Sun Lee et al: High-Perf., Transparent, and Stretchabte Electrodes Using Grapihene-Metal; 2013; Amer., Chem Soc,; pp. 2814-2821.

Jin-Seo Noh: Conductive Elastomers for Stretchable Electronics; 2018; Polymers 2016, 8, 123; doi: 10.3890/polym8040123: pp. 1-19.

Comionics; Cornixiting Cognionics Dry Conventional Wet Sensors; printed Apr. 26. 2017; pp. 1-3.

Florida. Research Instruments, In c4 FRI-2142-1; 19-Channel EEG Headband User Guide; printed .Apr. 26, 2017; pp. 1-11.

* cited by examiner

14A

Flat Prediction

Drawing of Tape Embodiment

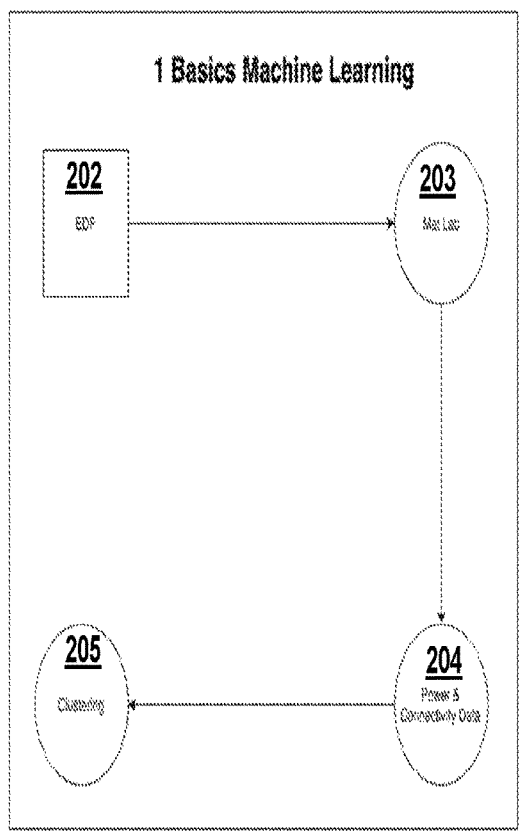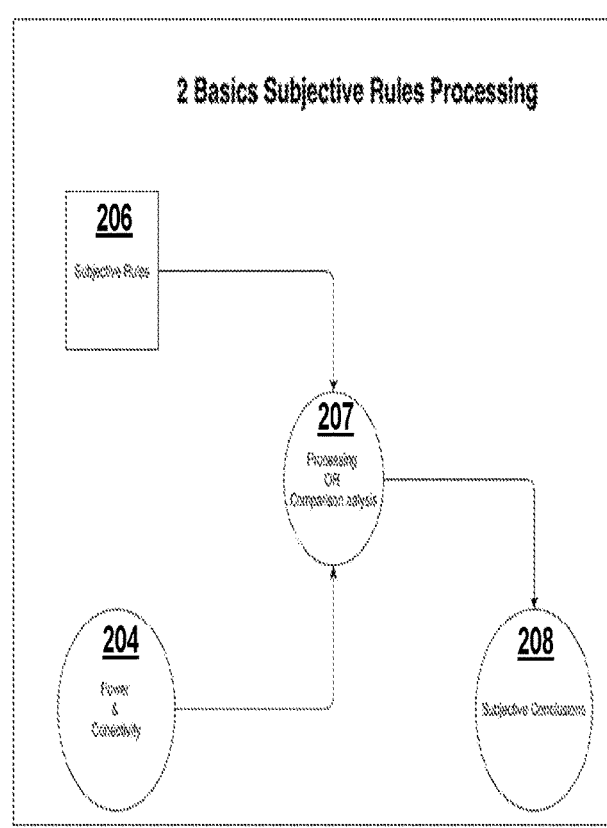
FIG. 17A
200
FIG. 17B
201

COMPUTER IMPLEMENTED METHOD FOR ANALYZING ELECTROENCEPHALOGRAM SIGNALS

CROSS REFERENCE TO RELATED APPLICATION(S)

This application is a divisional application of U.S. patent application Ser. No. 15/685,985, filed Aug. 24, 2017, which issued as U.S. Pat. No. 10,863,912 on Dec. 15, 2020, the entire contents of which are incorporated herein by reference.

FIELD OF THE INVENTION

The present disclosure generally relates to a method, and more particularly relates to a computer implemented method for analyzing electroencephalogram (EEG) signals using a plurality of sensors.

BACKGROUND OF THE INVENTION

Existing analysis of EEG signals primarily relies on recognition by individual experts and fails to take advantage of all the automation tools that might be incorporated in forming a useful analysis tool. A compendium of historical data that might supplement such expertise is not used in any formal fashion and normalization of such existing data to enable useful rendering of such supplementation has not been previously contemplated.

Existing methods to improve or verify data and further interpret such data suffer from poor efficiency or accuracy. A manual review of the data is very inefficient and could take quite a long time. Statistical methods can use simple thresholds, but suffer from poor accuracy and can cause deviant interpretations without appropriate analysis.

SUMMARY OF THE INVENTION

According to one embodiment of the present disclosure, a computer implemented method for of analyzing electroencephalogram signals can include capturing the electroencephalogram signals using a plurality of sensors configured to contact a skull, clustering the electroencephalogram signals using at least stored objective data and subjective data including patient profile data to provide clustered data results, and predicting one or more among a medical plan based on current practice parameters for the field of psychiatry or a diagnosis based on the clustered data results.

BRIEF DESCRIPTION OF THE DRAWINGS

The accompanying figures, in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 17A, FIG. 17B, and FIG. 18 are block diagrams of a portion of a system according to various embodiments of the present disclosure;

DETAILED DESCRIPTION OF THE INVENTION

Figure 1:
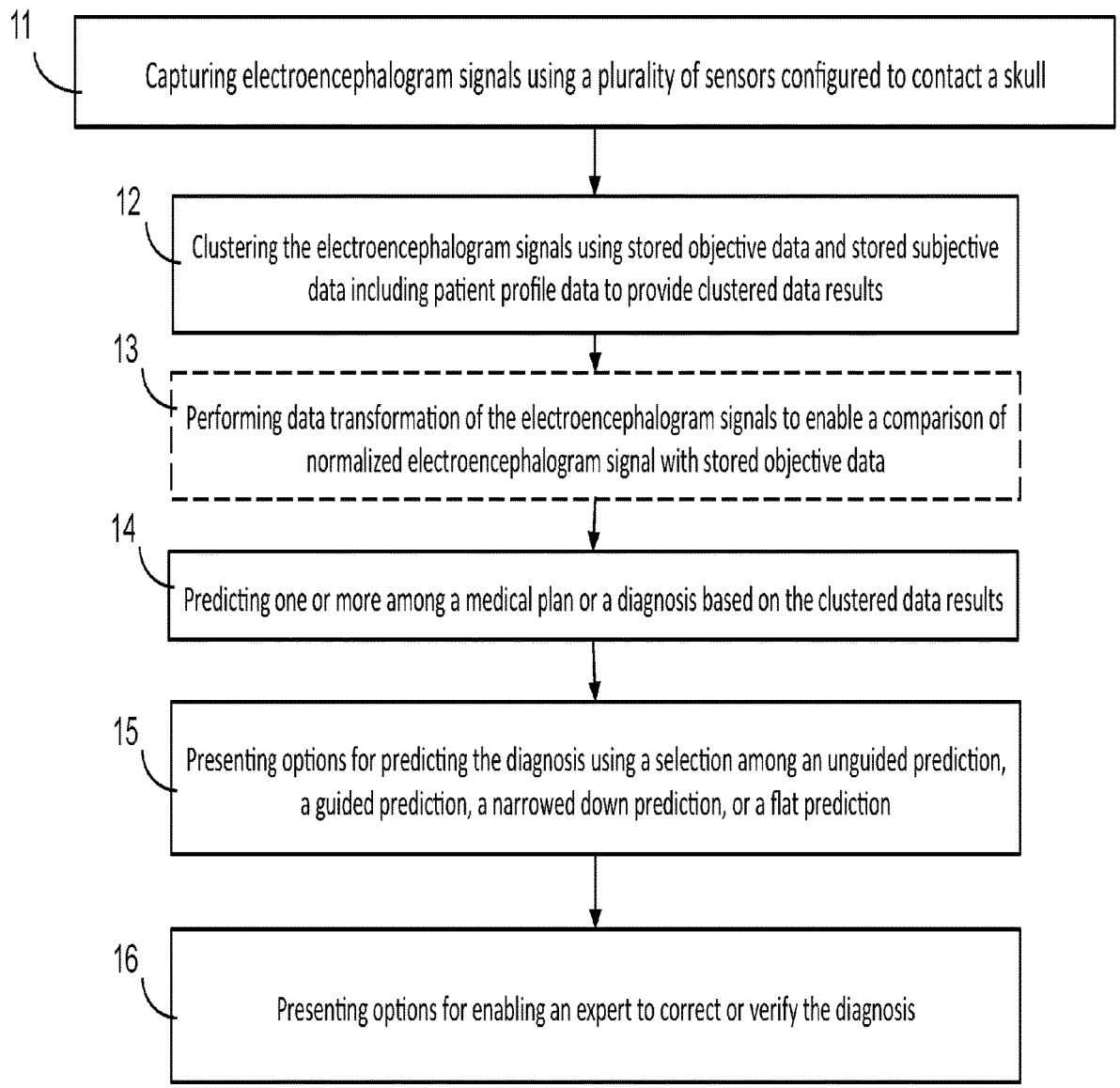
FIG. 1 is a depiction of flow diagram of a system or method for analyzing electroencephalogram signals using a plurality of sensors according to various embodiments of the present disclosure.

As required, detailed embodiments of the present disclosure are disclosed herein; however, it is to be understood that the disclosed embodiments are merely examples of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure and function. Further, the terms and phrases used herein are not intended to be limiting; but rather, to provide an understandable description of the disclosure.

According to various embodiments of the present disclosure, disclosed is a system and method for analyzing electroencephalogram signals using one or more sensors and more typically using a group of two or more sensors to enhance results beyond the results provided by existing monitoring systems. The embodiments utilize advanced neural network analysis (ANNA) to improve the accuracy and predictive analysis of brain related data to enable not only a monitoring tool, but also a clinical tool enabling rapid psychiatric diagnosis and treatment recommendation. Thus, a cloud based, machine learning, standardized diagnostic tool can increase, according to the embodiments, the timeliness and accuracy of brain related data for physicians and healthcare providers. Such tool utilizes ANNA to discover new patterns and associate them with certain ailments or treatments, and to make diagnostic predictions and risk assessments, to determine a necessity for psychiatric admissions. In some embodiments, ANNA can use specific triggers for outcome analysis. For example, certain aromas, sounds, or lighting can trigger particular expected outcomes or event related potentials.

ANNA ("Advanced Neural Network Analysis") is a clinical tool to assist in Quantitative EEG analysis, rapid psychiatric diagnosis, and treatment recommendations. ANNA can use a proprietary algorithm to analyze the deconstructed Mortlet Wavelet portion of an electroencephalogram (EEG) signal via a variation of K-Means Cluster Analysis. The description underlying the development and technical flow of ANNA will reveal several potential applications for this diagnostic tool.

ANNA's datasets include thousands of patients' Electroencephalograms (referred to as "objective data"), subjective data from the clinician and subject (or current patient), and functional data in the form of online performance testing. Referring to the flow chart of FIG. 1, a method 10 can begin by capturing electroencephalogram or EEG signals using a plurality of sensors configured to contact the skull at step 11. The process progress at step 12 by decoding raw data into clustering algorithms (algorithms used for machine learning). In other words, the method clusters the EEG signals using stored objective data and stored subjective data including patient profile data to provide clustered data results. The method can optionally perform (when necessary) data transformation of the EEG signals to enable a comparison of normalized EEG signals with stored objective data at step 13. Once the data transformation and clustering phase is done what follows is a prediction step 14 where a prediction of a medical plan and/or diagnosis is provided based on the clustered data results. Such prediction step can include global clustering (specific to ANNA) using various clustering algorithms, and prediction techniques based on the data patterns and decision maps ANNA learned so far from previous patients' analysis. Such prediction techniques can use any one among an unguided prediction, a guided prediction, a narrowed down prediction, or a flat prediction. At step 15, the method can present options for a user of ANNA for predicting the diagnosis using one (or more) of the aforesaid prediction techniques. At step 16, the method 10 can further enable the user (as a clinical expert) to correct or verify the predicted diagnosis presented by ANNA.

In clustering and prediction phase (steps 13 and 14) ANNA can take into account patient's personal details like age, gender, handedness, history, and pertinent medical issues. During the prediction phase, ANNA can collaborate with the clinician to come to a rational diagnosis and plan. One can simply define ANNA as a Supervised Machine Learning Assistant in EEG analysis. In general, the technical flow of ANNA's operations track the method 10 of the flow chart of FIG. 1 which includes data gathering or capturing, data transformation, clustering, global clustering, predicting, and correcting and/or verifying predictions from experts.

Figure 2:
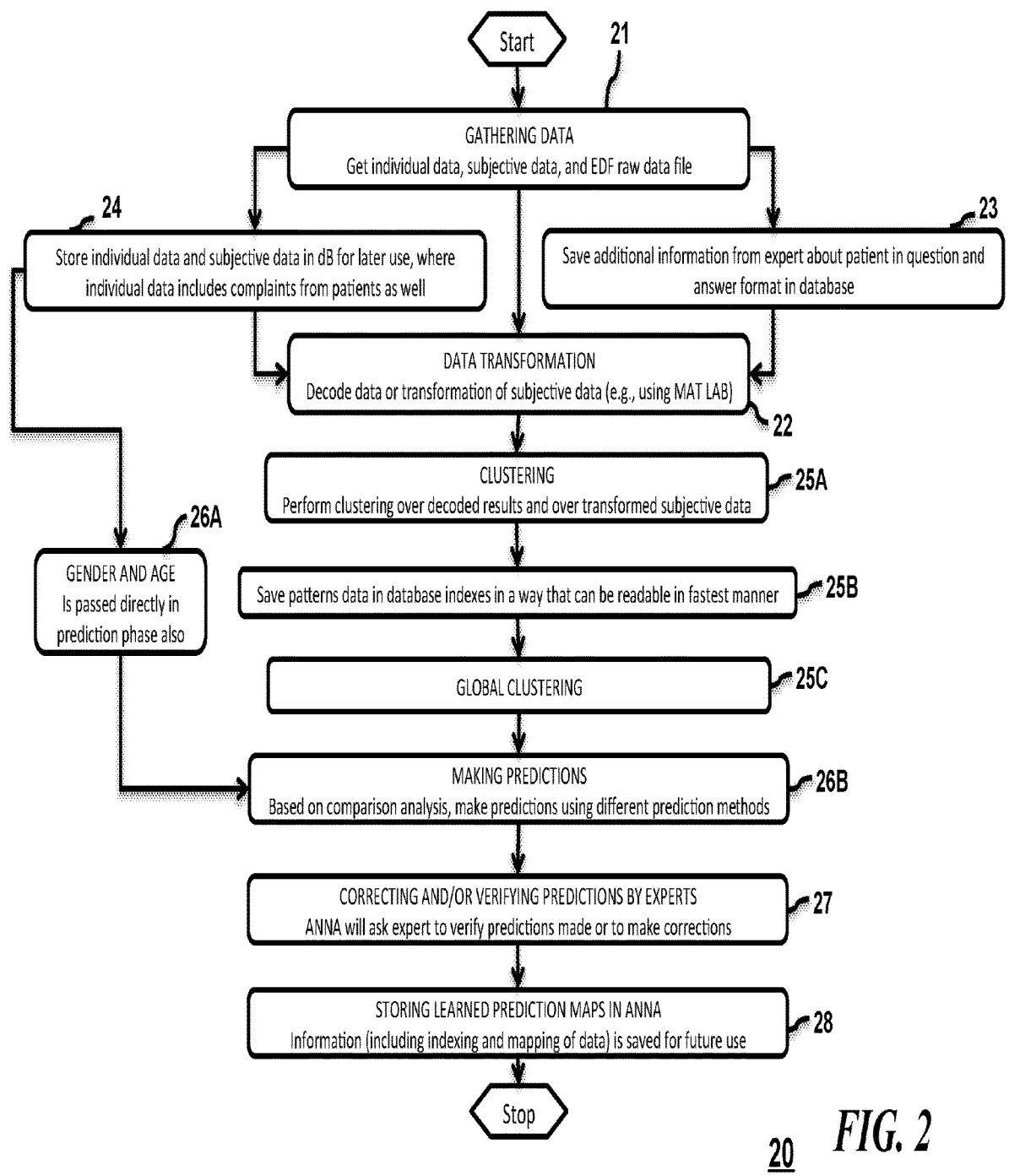
FIG. 2 is another depiction of flow diagram of a system or method for analyzing electroencephalogram signals using a plurality of sensors according to various embodiments of the present disclosure.

Referring to FIG. 2, another flow chart illustrates a method 20 in accordance with the embodiments in yet further detail. At step 21, the method gathers data including individual data, subjective data and EDF raw data files. Accordingly, a user can enter a patient's personal details like age, gender and subjective information, medication, any specific complaints, and some facts that might matter to EEG analysis. This information is later used in data clustering and in linking to the EEG data.

At step 22, data transformation includes decoding raw data and/or transformation of subjective data. At step 23, additional information from an expert about the patient in the form of questions and answers can be stored in a database and made available for the data transformation. Similarly, individual data and subjective data, which can include complaints from patients, can also be stored at step 24 in a database and made available for use for the data transformation step as well as for a subsequent prediction step (26B) via step 26A. Next, in some embodiments, the method 20 can include the step 25A of clustering over decoded results and transformed subjective data, which can be followed by step 25B of saving patterns of data in a database, and indexed in a way that could be readable or retrieved in a rapid manner. Method 20 can also perform global clustering at step 25C. At step 26, the method can make predictions based on comparison analysis made using different predictions methods. Some or all of the individual data (such as gender and age information) obtained at step 24 can be passed directly and utilized by the prediction step 26. Optionally, the method 20 can include the verification and/or correction stage 27 where expert information is used to verifying or correct predictions made by ANNA. Furthermore, as an iterative improvement process, learned prediction maps can be stored by ANNA for future use at step 28.

The data transformation 22 can include decoding raw data using several different alternative analysis methods such as Absolute power analysis, Relative power analysis, Amplitude Asymmetry connectivity analysis, Coherence connectivity analysis, Phase Lag analysis, Phase Shift analysis, Phase Lock analysis, current source density analysis, evoked potential analysis, or Low Resolution Electrographic Analysis.

Decoding raw data for "Absolute power analysis" can involve extracting Absolute power data for each Frequency by performing FFT (Fastest Fourier Transform) between the raw data (complex sine waves in theory) and a complex morlet wavelet sine wave for each frequency listed. A FFT is calculated using a dot product between both complex sine waves referenced above.

The background FFT and IFFT (inverse FFT) is performed to get back to the time domain from frequency domain and then power is averaged over the trial for each channels/montages.

Theta (4-8 Hz), beta (13-25 Hz), and gamma (80-120 Hz) are exemplary frequency ranges or bands that are analyzed for EEG signals. In a current embodiment, ANNA will have decoded results in the form of 5 vectors (a vector for each frequency band) which can be increased to 30 vectors or more with the number of dimensions equal to a number of channels/montages in raw data. In short, each element/dimension in the vector represents absolute power value for a particular channel/montage. Results displayed in the form of a vector with each channel/montage represent an element/dimension in the vector analysis. ANNA is processing data up to the channel/montages level, and data beyond that depends on the sampling rate and a number of trials (e.g., there are 17664 data points fora sampling rate of 256 with 69 trials of 1 second each) that are averaged. In the future, with additional processing power, ANNA can perform 3D analysis, and functional network analysis using a novel inverse solution to render the voxels necessary. A voxel represents a value on a regular grid in three-dimensional space. As with pixels in a bitmap, voxels themselves do not typically have their position (their coordinates) explicitly encoded along with their values. Instead, rendering systems infer the position of a voxel based upon its position relative to other voxels.

Decoding raw data for "Relative power analysis" involves a different process. After the absolute power extraction, what follows for relative power extraction is normalizing data for extracting relative data results. It is performed using log-based normalization using in theory the decibel method for normalizing data. To perform normalization against some base or relative parameters, a time window is selected from the range of raw data recording time. The resulting format is same as in Absolute power analysis.

Decoding raw data for "Amplitude Asymmetry connectivity analysis" involves decoding methods for connectivity results that are much different than the two analyses above, but results are not currently as accurate in implementation in comparison to other EEG tool results. Further refinements are needed. The connectivity result format for "Amplitude Asymmetry connectivity analysis" is much different than the two analysis above, but will operate more robustly after subjective data clustering is implemented.

Decoding raw data for "Coherence connectivity analysis" also uses techniques that are much different than the analysis used for Absolute Power Analysis or Relative Power Analysis. Although such techniques can be implemented with ANNA, results are not currently as accurate in implementation in comparison to other EEG tool results. After subjective data clustering is implemented, better results are anticipated.

Decoding subjective data can be straight forward to enable further processing such as clustering of such data.

Clustering is a field of machine learning technology used widely in many machine learning applications in data mining in a field of computer science. ANNA is mainly and specifically using a K-Means algorithm (one of the popular or common clustering algorithms out of many known clustering algorithms in computer science). There are few different flows (or sub areas) of implementing K-Means as per the requirement of data analysis. The K-Means algorithm in general enables ANNA to utilize data from the results of raw data decoding explained above and then pass the processed data to a clustering module and come up with clusters of data that will serve the purpose of identifying similarity patterns and eventually help in making predictions.

ANNA can utilize various clustering techniques in alternative embodiments, but the embodiments described herein use K-Means clustering. A K-Means algorithm in non-technical terms, is considered a proved theory of computer science which enables computers to classify information in the form of information clouds". K stands for a number of clusters, where the algorithm is provided with n observations and the algorithm classifies them in K number of clusters. Deciding a value for K depends on the type of data analysis requirement for a particular application and there are methods for deciding K dynamically also.

Decoded Data Clustering entails how the results from decoded data are mapped in clusters and what phases it goes through for making it usable for global clustering and flat predictions (or other prediction techniques if desired).

As explained above regarding "result format" in the decoding section above, the decoded results are available for each frequency bands at the level of channels/montages. Clustering is performed on these available results for each analysis methods using K-Means clustering methods explained above. However, in some embodiments, ANNA does not use a plain implementation of K-Means but there are some trial and error check mechanisms used to find the best K. The K-Means algorithm can be implemented in C# programming language and there can be one dependency library used for that implementation available through "Accord.Net". Note that the K-Means algorithm can also be implemented in other programming languages such as Python. After the clustering phase is over, a chosen K cluster provides information such as "to which cluster particular individual observation (decoded result) belongs" or "how the different cluster represents different group of observations with similarities". This information is saved in the ANNA database for later use in global clustering. It is important to note that the decoding phase is performed only on the individual readings for which analysis is performed while the clustering and global clustering is performed over all the observations known to ANNA or in simple words available in the ANNA database.

Subjective Data Clustering entails Subjective data processing to enable the availability of such data to other portions of the method or process.

Global Clustering entails clustering on decoded data clustering results. As explained in decoded data clustering, information is now available in forms that indicate how different observations are grouped together or to which group one particular patient observation belongs.

Clustering further entails statistical comparison and clustering of all results of all different frequency bands clusters to enable the find best matching patterns. The result of global clustering are patterns similar to patient's reading/observation being analyzed by ANNA. These patterns are useful in making predictions. Global Clustering on Subjective data clustering results can help further refine the process and enable more accurate predictions.

The prediction phase is the last phase of ANNA's analysis process and it is fairly simple. The prediction process takes matched patterns from the results of previous phases, find patient's references from patterns and simply makes predictions, which were made for those patients. However there are currently various prediction approaches implemented in an effort to provide insight and focus on a prediction method which is more efficient for future versions.

Predictions based on global cluster results can find a patient's references from patterns and simply make predictions which were made for those patients.

Figure 3:
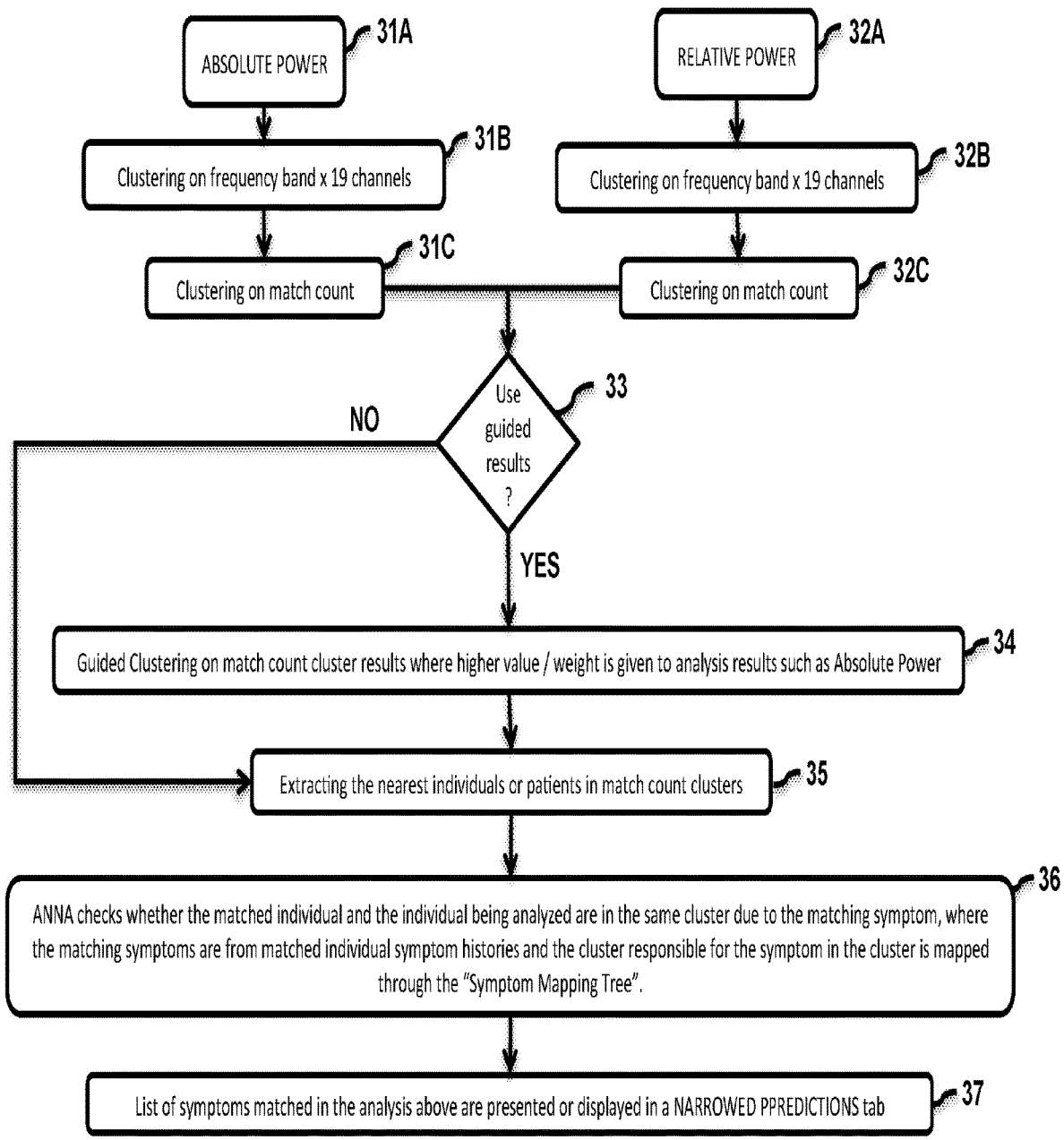
FIG. 3 is depiction of flow diagram of a portion of the system or method for analyzing electroencephalogram signals that performs a narrowed down prediction according to various embodiments of the present disclosure.
Figure 9:
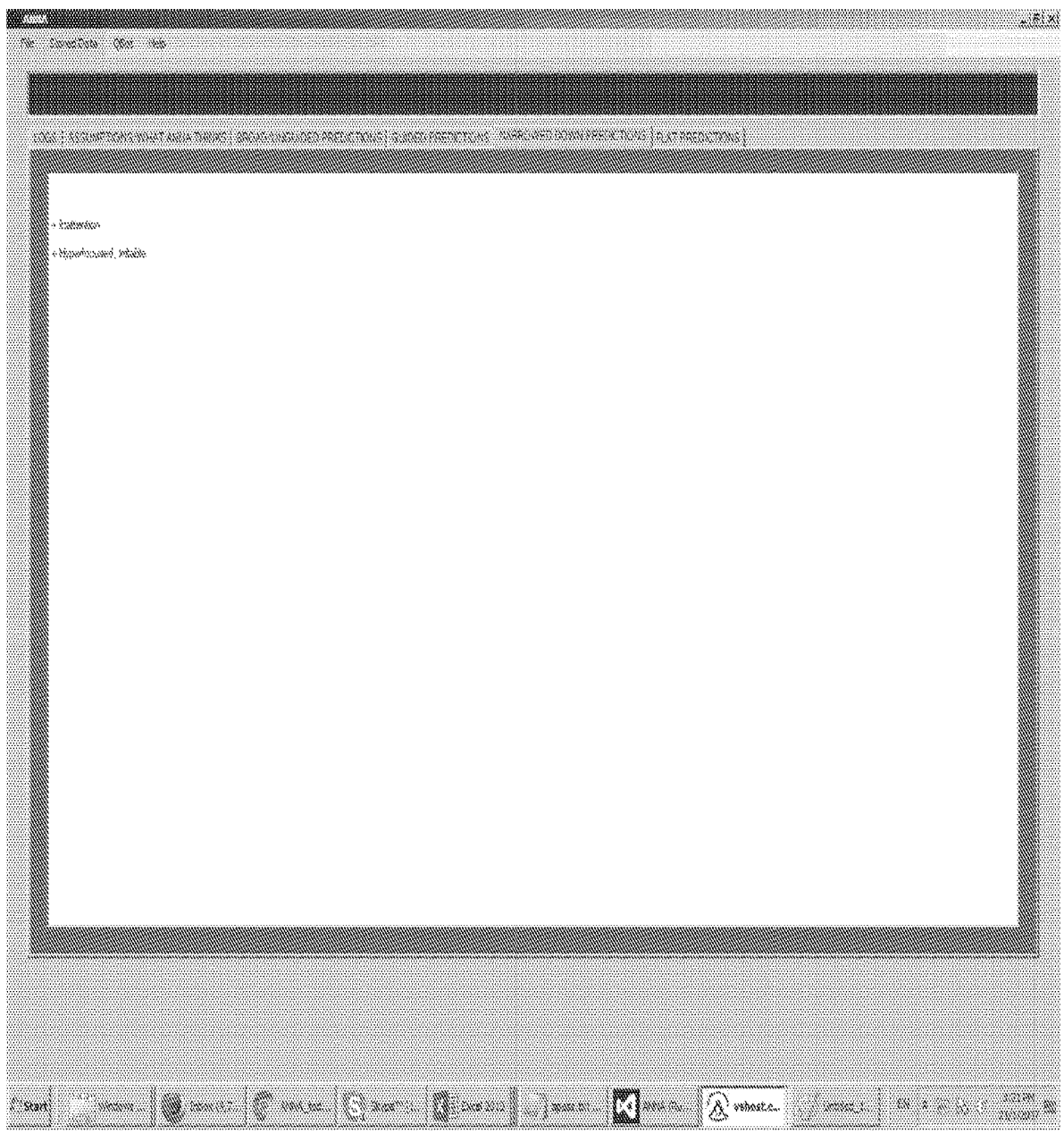
FIG. 9 is a depiction of a user interface for a narrowed down prediction according to various embodiments of the present disclosure.

FIGS. 3-6 illustrate various methods using various prediction techniques or methods in accordance with the embodiments. FIG. 3 illustrates a narrowed down predictive method using an absolute power analysis 31A, a clustering 31B over frequency bands (in one embodiment, over 19 different channels, but any number can be used), and a clustering at 31C based on a match count. Similarly, a relative power analysis 32A, a clustering 32B over frequency bands (in one embodiment, over 19 different channels, but any number can be used), and a clustering at 32C based on match count is done alternatively or simultaneously. Once the clustered results over the frequency bands are gathered, a determination of whether to use guided results is made at decision block 33. If guided results are to be used, then guided clustering is done on match count cluster results where higher value or greater weight is given to analysis results from the absolute power analysis for example at step 34 before extracting at 35 the nearest individuals or patients in the match count clusters. If guided results are not used at decision block 33, then the method directly extracts the nearest individuals or patients in the match count clusters at 35. At step 36, ANNA checks or confirms if the matched individual in the database and the individual being analyzed are in the same cluster due to the matching symptoms. The matching symptoms are from matched individual symptom histories and the cluster is further flagged or mapped with the new results through a "system mapping tree". At step 37, the list of symptoms matched through the analysis above are presented or displayed in one embodiment as part of a "Narrowed Down" predictions tab. The graphical user interface 90 in FIG. 9 provides a sample of a display of a "Narrowed Down" predictions tab providing the symptom predictions of "Inattention" or "Hyperfocused, Irritable".

Figure 4:
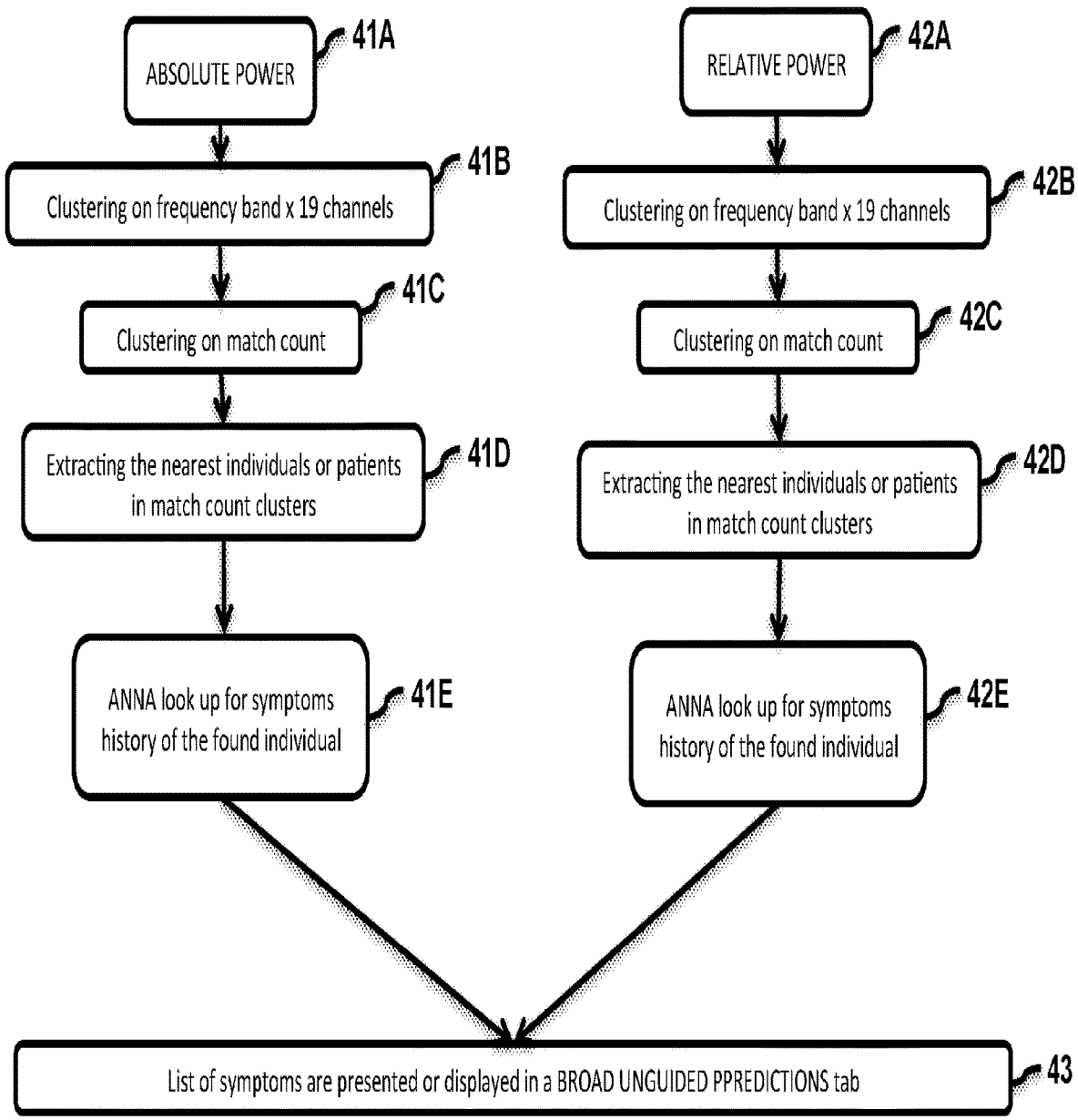
FIG. 4 is depiction of flow diagram of a portion of the system or method for analyzing electroencephalogram signals that performs a broad or unguided prediction according to various embodiments of the present disclosure.
Figure 7:
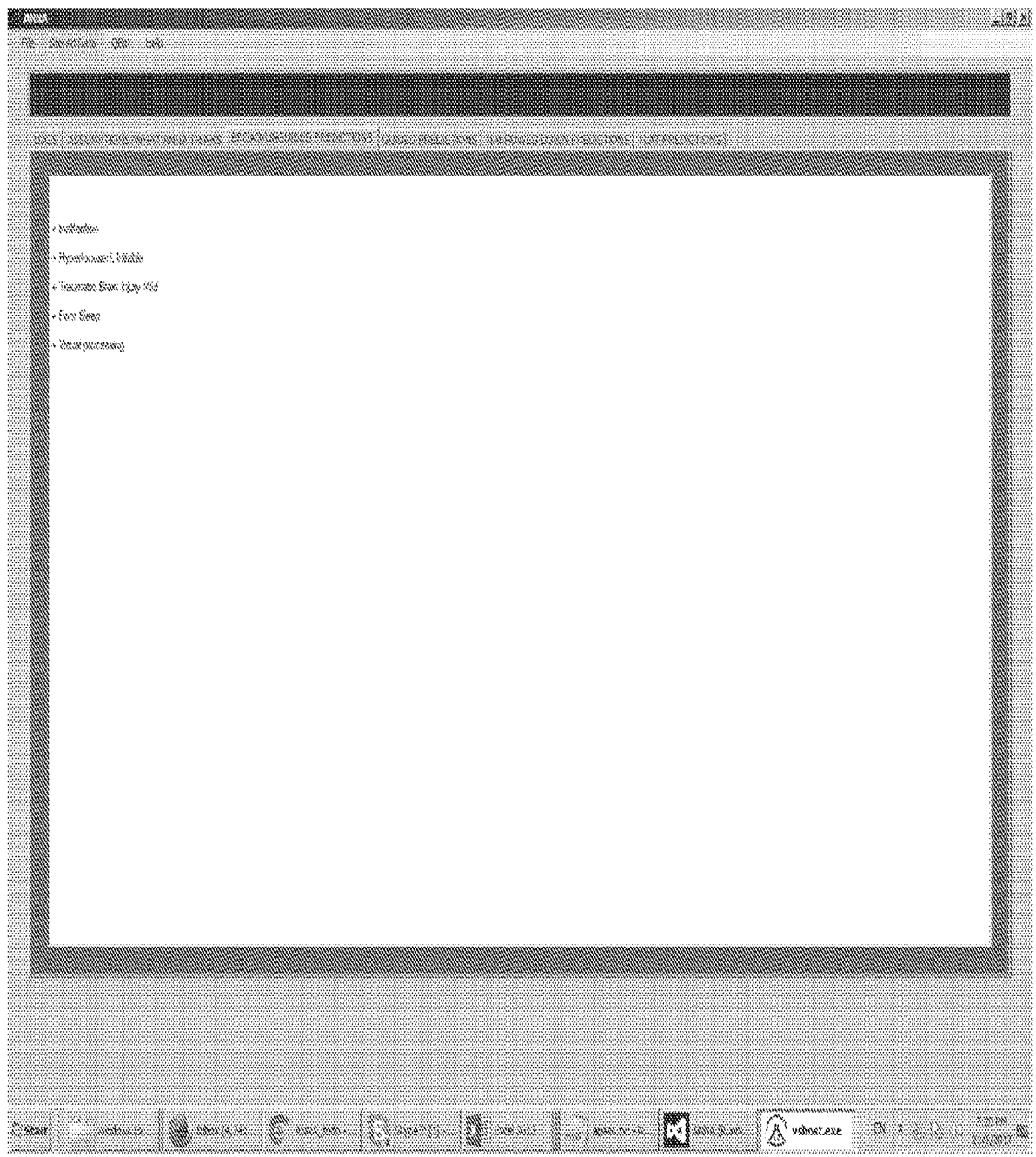
FIG. 7 is a depiction of a user interface for broad or unguided prediction according to various embodiments of the present disclosure.
Figure 8:
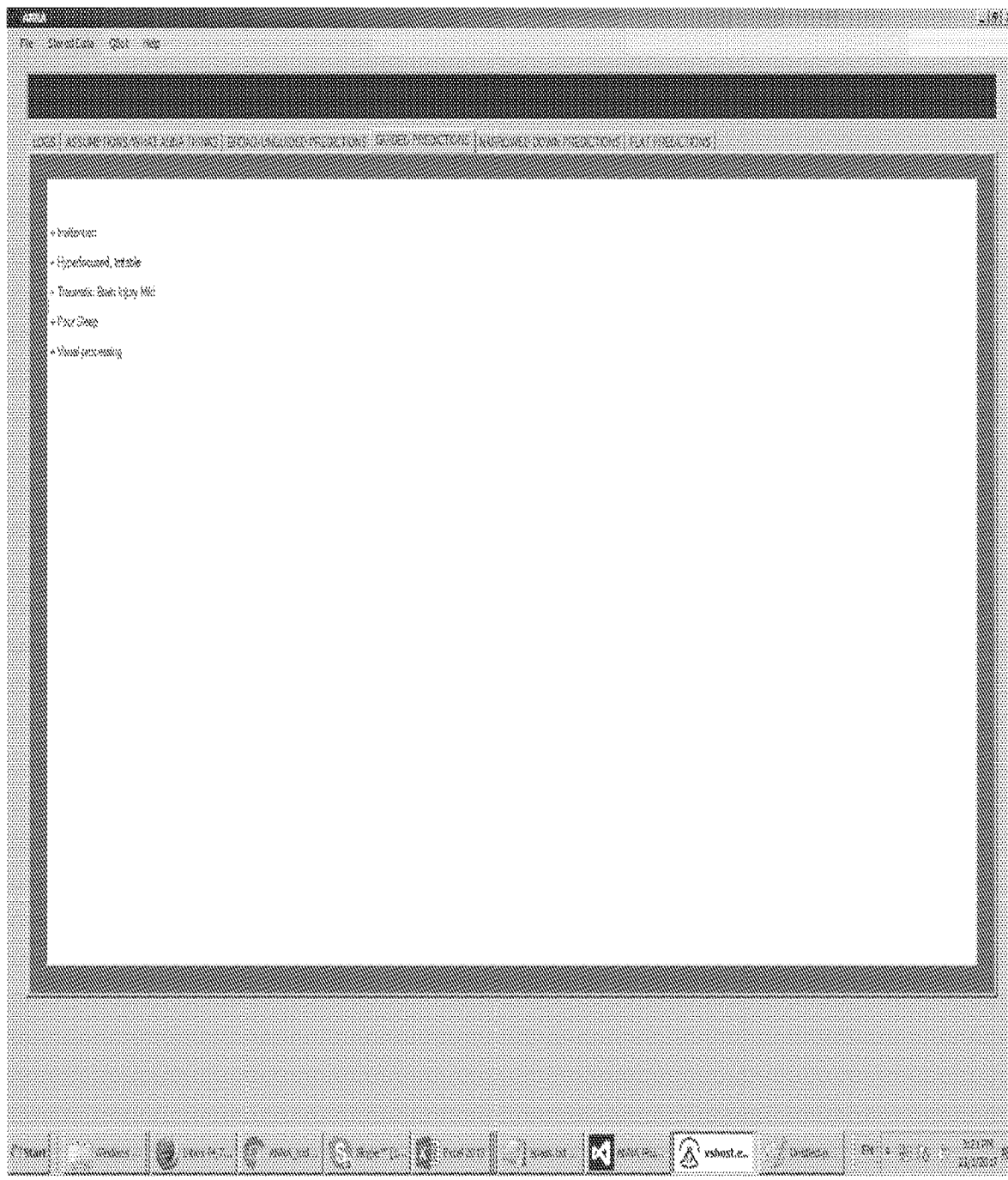
FIG. 8 is a depiction of a user interface for a guided prediction according to various embodiments of the present disclosure.

FIG. 4 illustrates a broad or unguided prediction method using an absolute power analysis 41A or a relative power analysis 42A or both. With absolute power analysis 42A, the method further performs a clustering 41B over frequency bands, a clustering at 41C based on a match count, an extraction 41D of the nearest individuals or patients in the match count clusters, and a look up 41E in ANNA's database for symptoms history of the found individuals. Similarly, with a relative power analysis 42A, a clustering 42B over frequency bands (in one embodiment, over 19 different channels, but any number can be used), a clustering at 42C based on match count is done alternatively or simultaneously, an extraction 42D of the nearest individuals or patients in the match count clusters, and a look up 42E in ANNA's database for symptoms history of the found individuals. In this particular approach, the generation of a list of symptoms is unguided and presented at 43. The presentation can be a display of a Broad or Unguided Tab on a graphical user interface (GUI) 70 as illustrated in FIG. 7. In this example, the Unguided Tab of the GUI 70 displays the symptoms of Inattention, Hyperfocused-Irritable, Traumatic Brain Injury Mild, Poor Sleep, and Visual Process.

Figure 5:
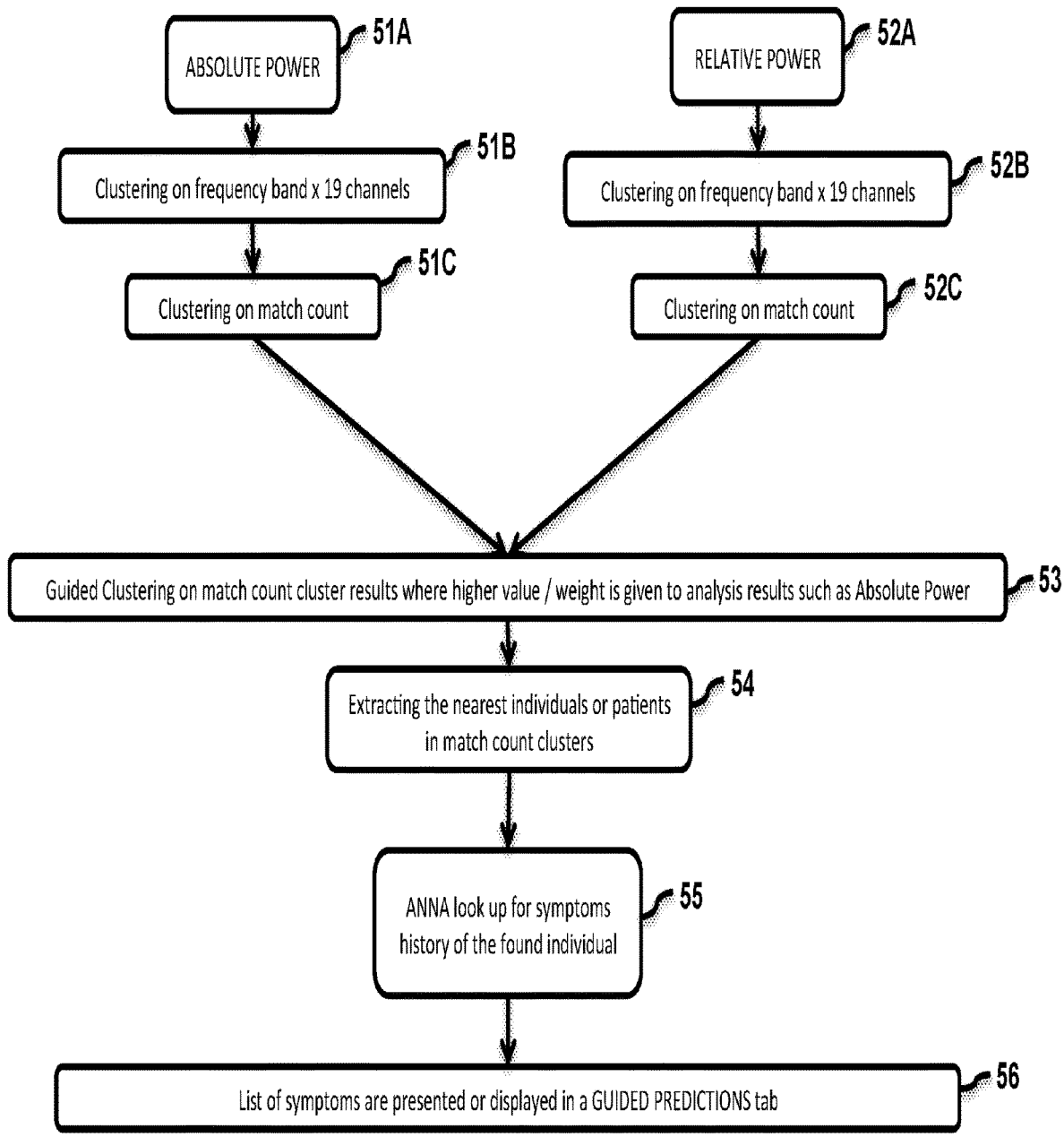
FIG. 5 is depiction of flow diagram of a portion of the system or method for analyzing electroencephalogram signals that performs a guided prediction according to various embodiments of the present disclosure.

In some embodiments, the Guided Prediction method as illustrated in the method 14C of FIG. 5 includes a slightly different approach by taking same matched patterns results from previous phases but instead of choosing predictions it gives weight to patterns which are the results of clusters of analysis methods which are more valuable or important from the EEG experts point of view in making decisions after observing patient's readings. More particularly, the method 14C performs an absolute power analysis at 51A, clusters on frequency bands at 51B, and clusters on the match count at 51C. Method 14C simultaneously or alternatively performs a relative power analysis at 52A, clusters on frequency bands at 52B, and clusters on the match count at 52C. Once the clustered results over the frequency bands are gathered, in this guided prediction method then guided clustering is performed on match count cluster results where higher value or greater weight is given to analysis results from the absolute power analysis for example at step 53 before extracting at 54 the nearest individuals or patients in the match count clusters. For example normally EEG experts would give more weight to Absolute power results than relative power results. However it is configurable in ANNA, so a user of ANNA can decide what weight to give to a particular analysis method. For example, the weighting can range from 1 to 10. At step 55, ANNA checks or confirms if the matched individual(s) in the database and the individual being analyzed are in the same cluster due to the matching symptoms. At step 56, the list of symptoms is presented such as on a Guided Predictions Tab of a GUI 80 of FIG. 80. For example, the user interface 80 illustrates a guided predictions tab which displays the potential symptoms of "inattention, Hyperfocused, Irritable, Traumatic Brain Injury Mild, Poor Sleep, Visual Processing, etc.".

In some embodiments, the Narrowed Down Prediction method 14A as illustrated in FIG. 3 and discussed above can be considered a filtered version of global predictions made, where techniques used for filtering are based on best match logic. In simple terms, the narrowed down prediction method just drops the predictions that are not best matches and may not be as accurate as other prediction techniques depending on ANNA's assumptions.

Figure 6:
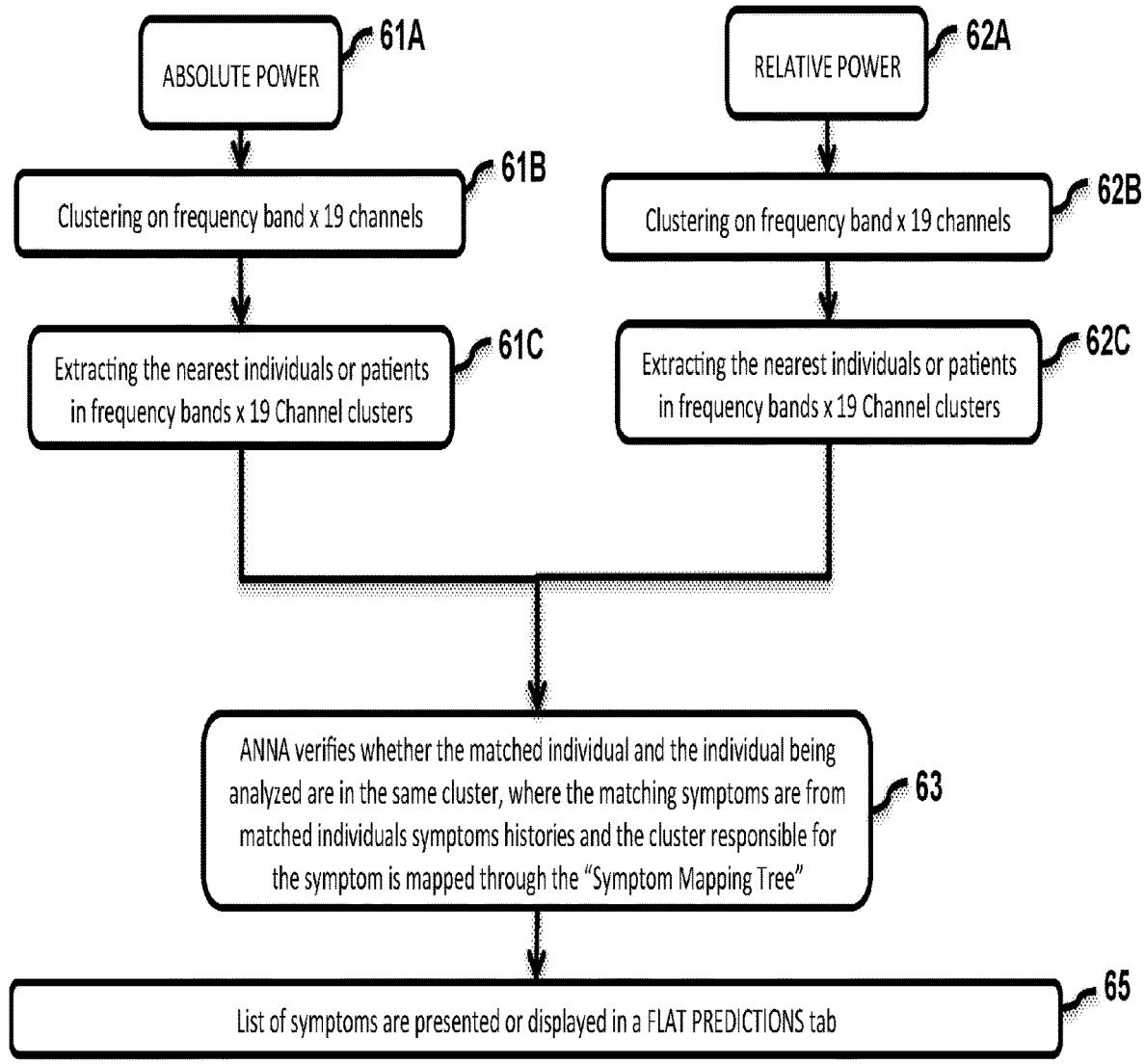
FIG. 6 is depiction of flow diagram of a portion of the system or method for analyzing electroencephalogram signals that performs a flat prediction according to various embodiments of the present disclosure.
Figure 10:
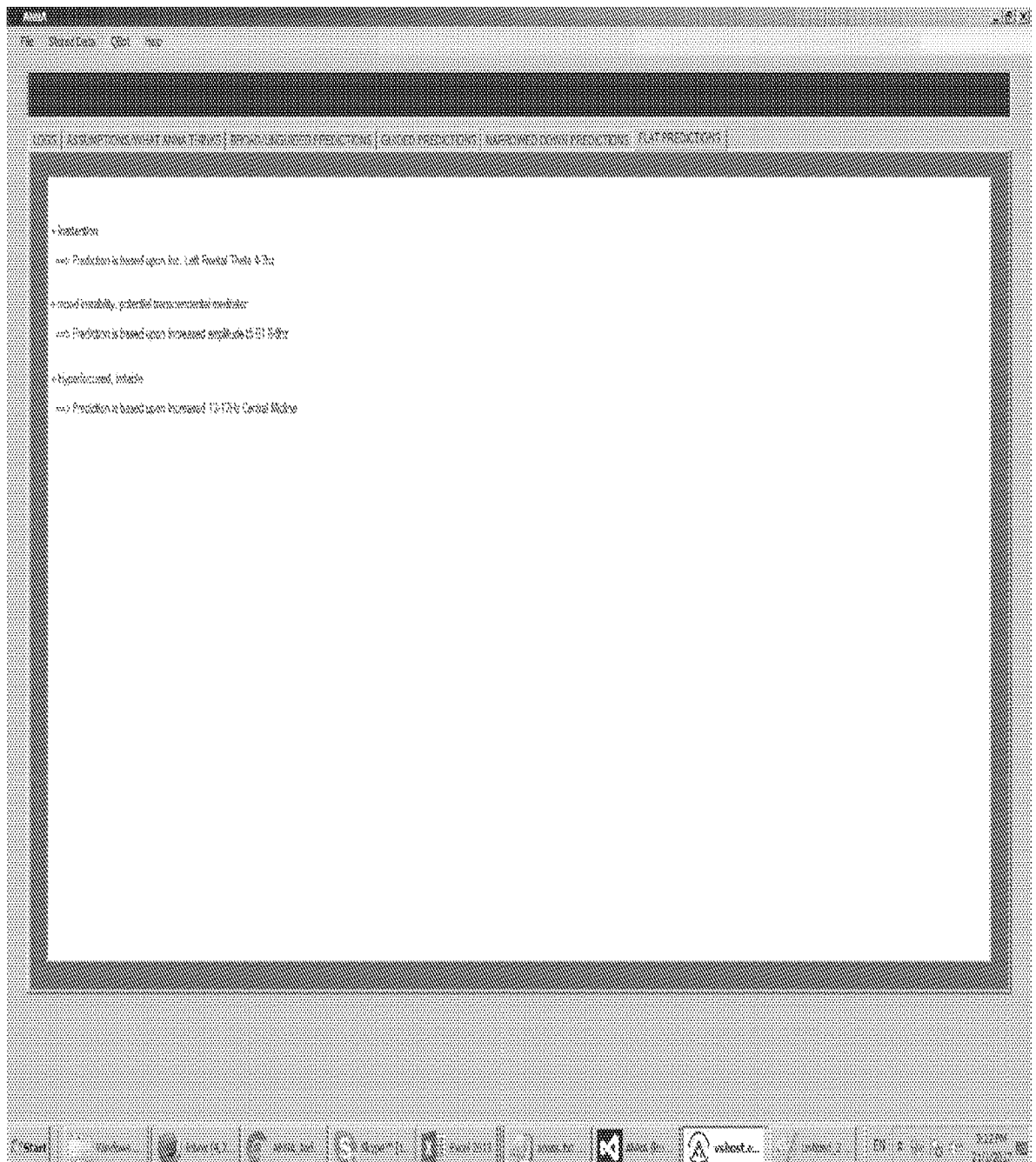
FIG. 10 is a depiction of a user interface for a flat prediction according to various embodiments of the present disclosure.

Referring to FIG. 6, a method 14D illustrates a flow chart where Flat Prediction analysis is used. The flat prediction method 14D can have quite a different flow of making predictions or a flow that is very flat, hence the given name of "Flat Predictions". This is a straight forward implementation of making predictions as part of the port process after clustering while the above two methods were custom implementations specific to ANNA. While the "Flat Predictions" method is straight forward, it has disadvantages of potentially being noisy as the number of observations grows in the ANNA database. More particularly, the method 14D performs an absolute power analysis at 61A, clusters on frequency bands at 61B, and clusters on the match count at 61C. Method 14D simultaneously or alternatively performs a relative power analysis at 62A, clusters on frequency bands at 62B, and clusters on the match count at 62C. Once the clustered results over the frequency bands are gathered, a flat prediction is performed at 63 and a list of systems based on the flat prediction is presented or displayed at 65. Flat predictions work by simply deriving patterns directly from decoded cluster results so it skips global clustering done in the other analysis methods. The comparison done by flat prediction analysis depends on making predictions from the same clusters from patient observations using the level of frequency bands signal. Thus, a user interface 92 as shown in FIG. 10 might display a Flat Prediction Tab showing a symptom of "Inattention" based on left frontal Theta wave between 4-7 Hz, a symptom of "mood instability" and "potential transcendental meditator" based on increased amplitude t5.01 (left Temporal Lobe T5 and memory encoding with semantic tasks with respect to the Occipital Lobe 01) in the 8-9 Hz range, and symptoms of "Hyperfocused" and "Irritable" based upon increased 13-17 Hz Central Midline signaling. The other methods may provide similar results, but not always.

Figure 11:
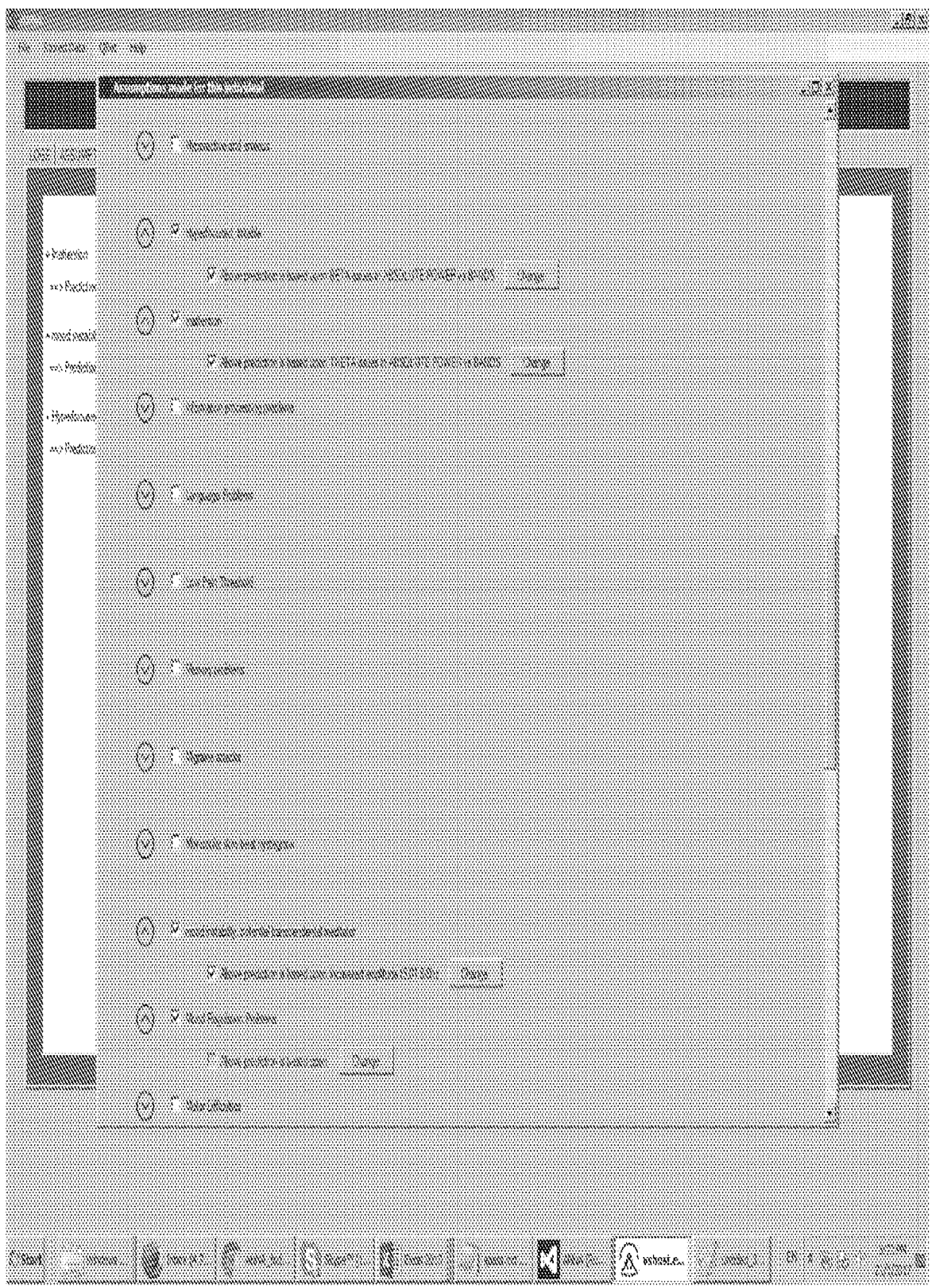
FIG. 11 is a depiction of a user interface for correcting and/or verifying a prediction by or from experts according to various embodiments of the present disclosure.
Figure 12:
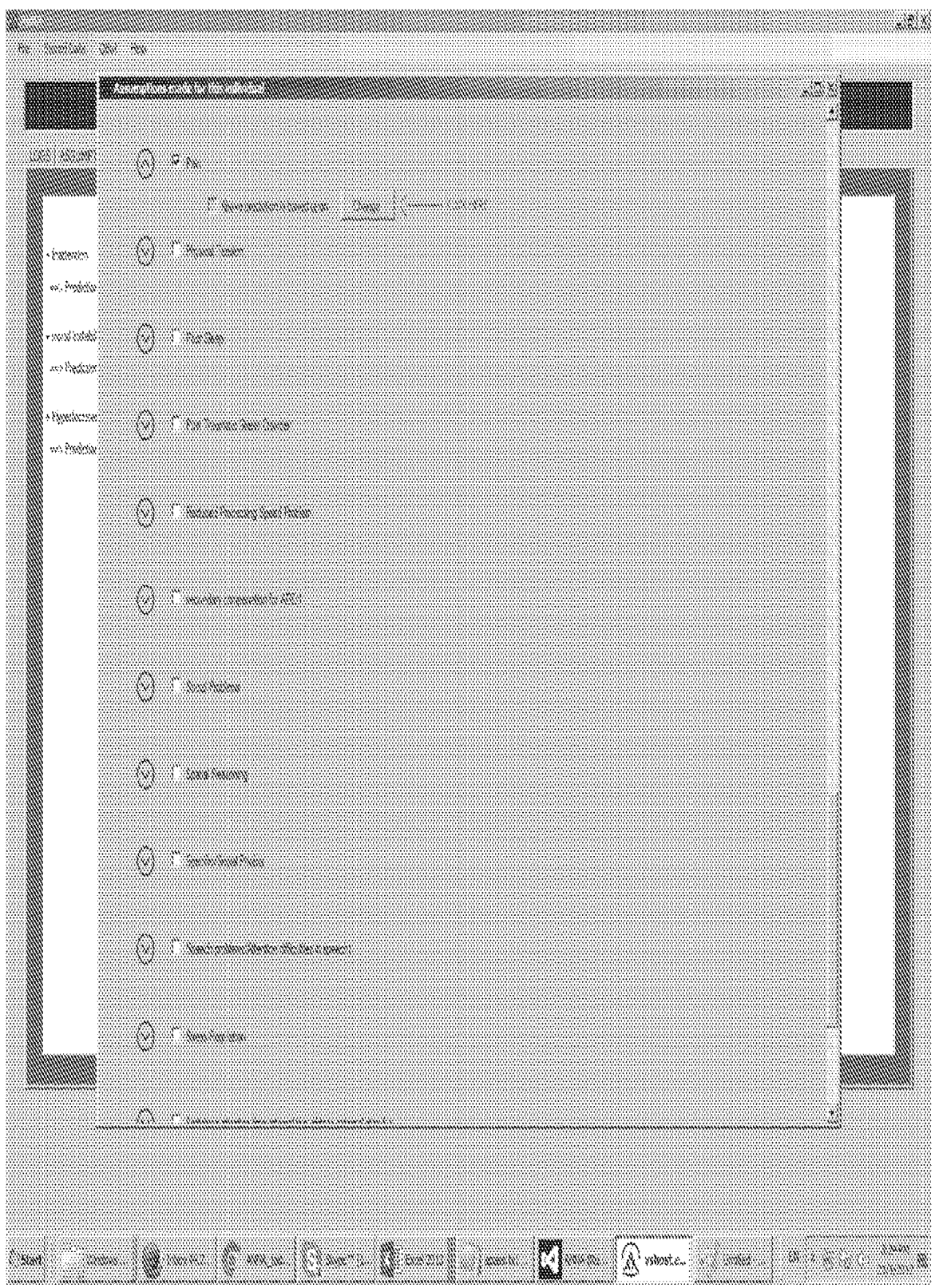
FIG. 12 is a depiction of a user interface used for prediction mapping according to various embodiments of the present disclosure.
Figure 13:
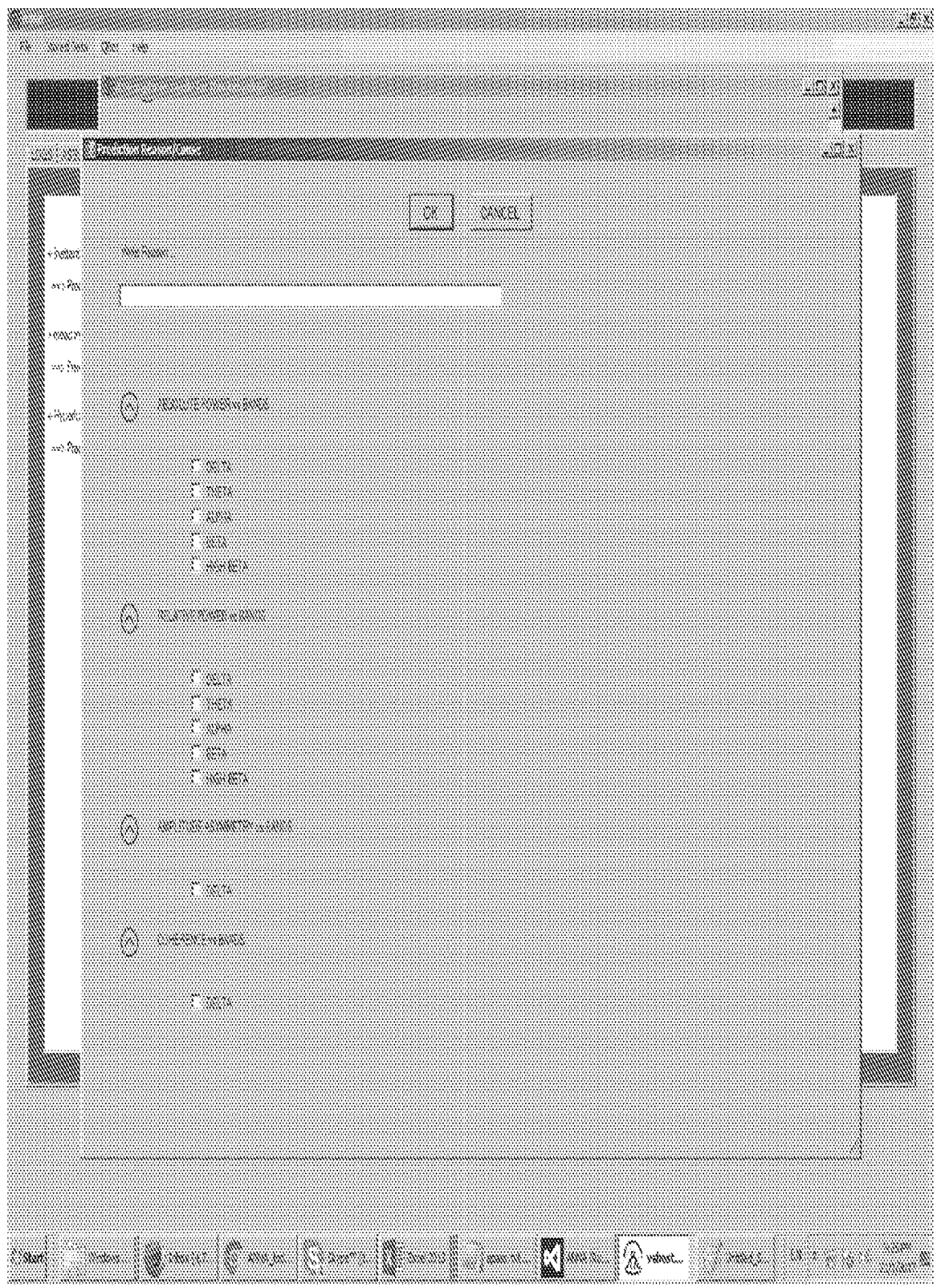
FIG. 13 is a depiction of a user interface for annotating or logging reasons for the predictions according to various embodiments of the present disclosure.

Correcting and/or verifying predictions from experts (as noted in step 16 of FIG. 1 or step 27 of FIG. 2) is a very crucial phase from the perspective of verifying predictions from EEG experts as this is how ANNA learns from experts in a form of Artificial Intelligence. In this phase, the user is supposed to verify or correct the predictions ANNA made, add predictions that ANNA possibly missed in the event ANNA's database failed to previously include sufficient learned information to make such predictions yet. From a practical standpoint, the correction or verification phase can be implemented in one or more graphical user interfaces as shown in FIGS. 11-13. GUI 93 of FIG. 11 provides a listing of assumed symptoms for a particular observed individual or patient. The GUI 93 can include a listing of assumed symptoms for a particular observed individual where each of the symptoms can be selected or de-selected based on expert knowledge of the GUI user to correct or verifying the assumed symptoms shown. In some instances, the listed symptom can include an option that acknowledges that a predicted symptom was based on a particular theory or analysis such as a flat based prediction such as based on "BETA issues in ABSOLUTE POWER vs. BANDS". As shown further in GUI 94, if the expert wants to specify or change the basis of the prediction, then there is an option in the form of a button to change such basis. For example, if the basis of the symptom of "Insomnia" was wrong or unspecified, the GUI enables the user to change the basis. Referring further to the GUI 95 of FIG. 13, the GUI 95 can include a pull down menu, a selectable menu, or text entry field to provide expert based symptoms. Note that data can also be entered into to text entry field using other data input mechanisms and engines that utilize speech to text entry or smart artificial intelligence engines such as IBM's Watson as an interface to the ANNA system. Although Watson may have certain data useful for the overall process, Watson will not have specific data for brainwave analysis and patient assessment that will be specifically used herein. For example, pre-set selectable options for describing or setting the basis (or additional basis) of an assumed basis for a symptom such as "Pain" (from FIG. 12) could be based on Absolute Power over bands or Relative Power over bands, or Amplitude asymmetry over bands, or coherence over bands. The particular bands that form the basis of such assumption can also be noted (Delta, Theta, Alpha, Beta, High Beta, etc.). If there is another basis that is not listed as a pre-selected option, the GUI 95 enables the user to write in a basis using text in a text field.

Prediction mapping in ANNA for patients are stored in ANNA's database enable the system to improve its ability to deliver better and accurate results. Prediction mapping is information that maps a patient's symptom with the cause for that symptom which can be predictably associated with certain signaling profiles known by experts. For example, if the patient is anxious, then the cause can be presumed to be high beta issues as might be mapped in ANNA's database. Prediction mapping entries are stored prior to displaying such resultant predictions to a user and updated after the corrections are made by experts so the system will be considered robust and in some embodiments always in a state of improvement and reliability. As the system is configured to frequently or always verify, correct and supply additional information (if applicable) in this phase, the prediction mapping in ANNA inherently makes better predictions for future patients. In some respects, ANNA is considered self-improving or self-healing due to this most important interface with experts where ANNA could take information from humans and learn.

Extensions of the outputs that ANNA can provide are numerous. In some embodiments, the outputs that ANNA provides can include output reports including information that an expert, physician or clinician would need to render the correct insurance billing codes, and subsequent steps to legally maximize billing under a current regime or could employ a protocol with the least amount of risk. The system can also compare previous treatment success outcomes and make predictions regarding the chances of success of a given plan. The system can also automatically program an EEG-Biofeedback protocol into a user end of the system and run this protocol on any device that has Java-script. Such device can include a desk top computer, a smart phone, lap top computer, or tablet as examples. In future embodiments, the device biofeedback protocol can be incorporated into augmented reality or virtual reality devices currently or contemplated to be introduced into the market. The device will support the training aspect of the entire system and make recommendations regarding the placement of electrodes or arrays of electrodes in cap form or in tape designs referred here as "Neurotape". The placement of the electrodes in caps or neurotape or whatever form factor can be based on previous outcomes, subjective data and stored data to enable the user or practitioner to appropriately adjust the placement of such electrodes on a skull or scalp. Aspects of Neurotape have its own utility and independently improve specific issues of EEG Coherence without having to use Neurotape with ANNA. The usefulness of Neurotape is only further magnified and made apparent with used in conjunction with ANNA. That this tape would be disposable and used as per directions of ANNAs system.

Although the use of ANNA is not limited for use with a particular implementation of a plurality of electrodes, Neurotape will enhance signaling and results. Other embodiments for a plurality of electrodes or sensors can include a fixed cap or a customized cap that can be printed for each individual making sizing more consistent. Such a printed cap can be made or flexible material or of more durable or hardened materials and is feasible today with current 3D printing techniques. In some embodiments, the entire system can work on "NeuroJavascript" which will be cross platform. In some embodiments, the system can also include a feedback system based on dimming a user's screen and raising and lowering the volume of the device rather then some additional piece of software that enables feedback. Thus, the feedback mechanism can be simple and avoid additional hardware costs if the hardware already includes visual and/or audio outputs. Again, Neurotape can be used with or without ANNA. In some embodiments, Neurotape can be analogous to a customizable Breathe-right strip that corrects a condition detectable by EEG signaling. This tape can be mass-produced and the directions for each disorder printed on the instructions. Once a condition is determined or suspected, the Neurotape can be appropriately placed on the skull to help rectify or alleviate a particular detected or suspected ailment or condition. Using ANNA, the predicted ailment or condition and corresponding prescription to rectify such ailment or condition can be tailored making appropriate neural connections using Neurotape.

Figure 14A:
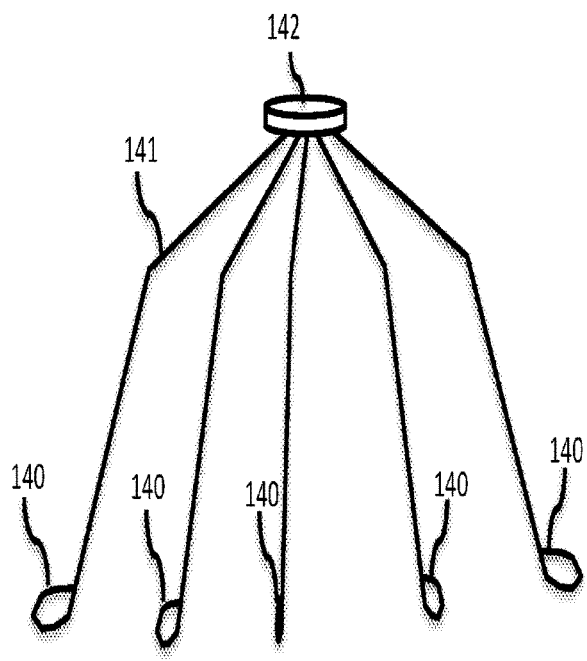
FIGS. 14A, 14C, 14D, and 14E depict illustrations of various electrode arrays
Figure 14B:
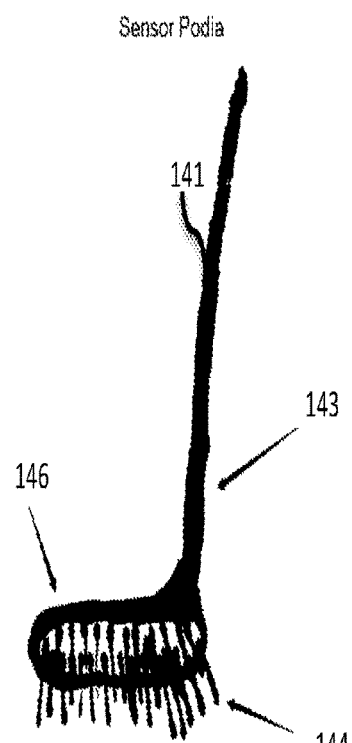
FIG. 14B is an illustration of a form of electrode shown in further detail that is used in at least one of the plurality of sensors that captures the electroencephalogram signals according to various embodiments of the present disclosure.
Figure 14C:
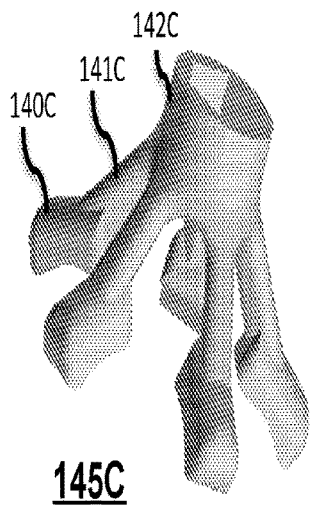
Figure 14D:
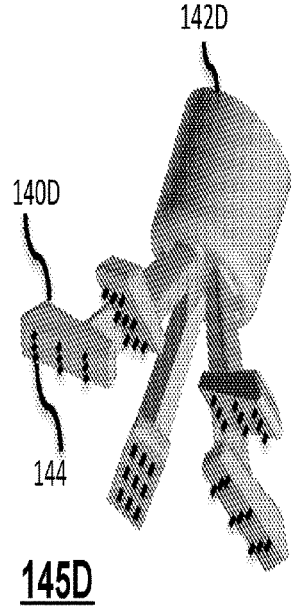
Figure 14E:
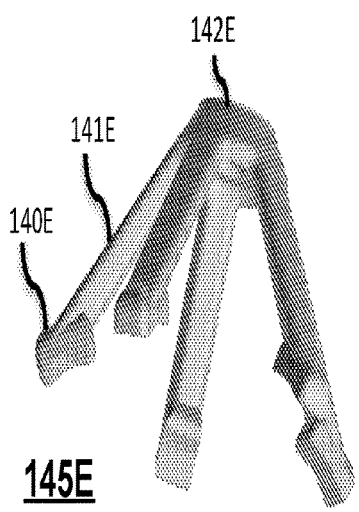

Referring to FIG. 14A, a sensor array 145 illustrates a plurality of electrodes 140 or sensor podia all coupling to a control hub 142 via a connector leg 141 that includes an internal conductive connector between the electrode 140 and the control hub 142. The array 145 can be placed on a users head and each electrode 140 can be placed appropriately at designated locations on the user's head. The electrode 140 is shown in further detail in FIG. 14B and can be used in conjunction with ANNA. Although any conventional EEG electrode can be used with ANNA, better results can be provided using an electrode that will provide better contact with the scalp or skull and that further has inherent interference immunity characteristics due to its structure and composition. In this regard, the electrode 140 can include a plurality of prongs or microfilaments 144 that can bury through a thicket of hair to provide direct contact with the scalp or skull. The microfilaments 144 can be encased or covered by a coating (such as graphene) to provide a Faraday cage 146 to make the signaling obtained from the microfilaments 144 more immune from external interference. Similarly the connector leg 141 can be coated with graphene or a graphene composite. The leg 141 and Faraday cage 146 can be formed of an integrated graphene or graphene composite body. More particularly, electrode 140 can be part of the plurality of sensors (145) that are electroencephalogram sensors having prongs extending less than a particular distance from the central hub 142 at equidistant angles from one another and forming podia extending outwards at an angle from the shaft and in some embodiments further formed of graphene. In some embodiments, the EEG sensors can each have prongs extending less than 2 centimeters from the central hub 142. In some embodiments, the EEG sensors (145) can each have prongs forming podia extending outwards at a complement of a 37-degree angle (143-degree angle) from the shaft or connector leg 141. In one particular embodiment, the EEG sensor or electrode have prongs extending less than 2 centimeters from a central hub at equidistant angles from one another and forming podia extending outwards at a 143 degree angle from the shaft and further being formed of graphene. In some embodiments, the podia can extend outwards from the shaft at angles ranging from 135 to 150 degrees from the shaft. Each senor 140 can also have microfilaments 144 extending from the base of the podia (140) and can contain individual faraday cages (146) on each podia. The individual electrodes in the plurality of electrodes can be connected to each other and/or to a signal processing device via a wired or wireless connection. In the case of a wireless connection, any number of wireless protocols such as Bluetooth, WiFi, Zibbee or others can be used to provide such wireless connection as needed. Note, in a wireless version, each sensor 140 would wirelessly couple to the central hub 142 (or other signal collection point) without the need fora wired connection (141). FIGS. 14C, 14D, and 14E, depict similar alternative embodiments to the sensor array 145 of of FIG. 14A including sensor arrays 145C, 145D, and 145E respectively. Sensor array 145C of FIG. 14C includes a central hub 142C, a shaft or leg member 141C, and an electrode or podia 140C. A bottom portion of each of the podia 140C can be curved to ergonomically fit a user's scalp, skull or head. Further note that the central hub 142C in this embodiment can be a receptacle for receiving a central controller (not shown) that electronically couples to the conductors in the electrodes 140C. FIG. 14D depicts the sensor array 145D that includes a central hub 142D, a shaft or leg member 141D, an array of electrodes or podia 140D, and further depicts the microfilaments 144 on each electrode 140D. FIG. 14E depicts the sensor array 145E that includes a central hub 142E, a shaft or leg member 141E, and an array of electrodes or podia 140E. Again, a bottom portion of each of the podia 140E can be curved to ergonomically fit a user's scalp, skull, or head.

Figure 15:
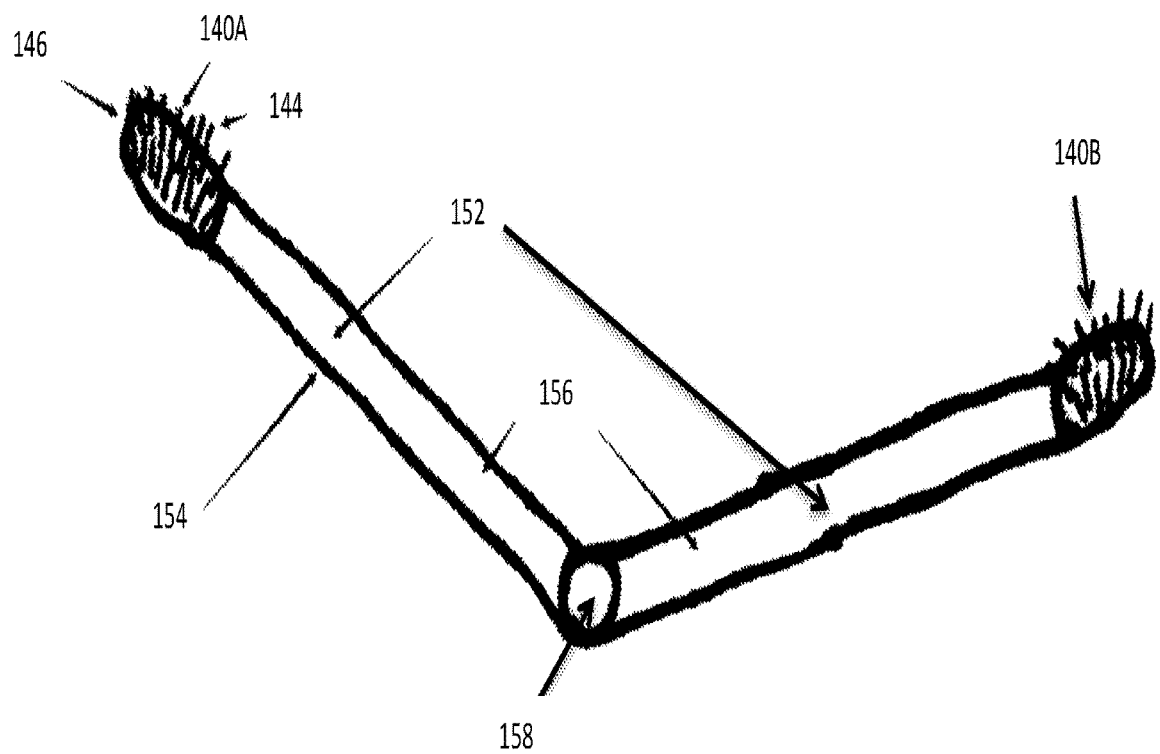
FIG. 15 is an illustration of a tape or sensor array optionally used in conjunction with the systems and methods according to various embodiments of the present disclosure.

Referring to FIG. 15, the electrodes 140A and 140B (similar to electrode 140 of FIG. 14B) or other EEG electrodes can be incorporated into a tape design 150 that forms at least a pair of electrodes coupled to each other to enable better connectivity between specific sites associated with known brain signaling or characteristics that can be extracted from EEG signaling. The tape design 150 can embodied as the "Neurotape" discussed above. The tape design 150 can include an adjustment element 158 (such as a hinge) enabling the user or clinician to modify the placement or location of the separate electrodes 140A and 140B. In some embodiments, the adjustment element can also alternatively have an accordion type feature to adjust the distance between the electrodes 140A and 1406 or the length of their respective legs or connectors. The tape design 150, in some embodiments, is a pure passive device that enables greater interconnection or connectivity between specific brain sites or even brain regions. As noted above, use of the electrode 140 will further enhance the ability to provide adequate connections to the appropriate and respective sites on the scalp or skull due to the structure and composition of the electrode 140. The microfilaments 144 provide better connections to the intended or desired sites and the graphene coating on the portions 152 of the electrodes 140A and 140B (and optionally on the Faraday cage 146) further reduce interference from extraneous signals that can potentially interfere with the desired EEG signaling. In some embodiments, an external portion or outer body portion 154 of the tape design 150 would be formed of non-conductive material. The tape design 150 can also include adhesive 156 to retain the tape design 150 in the desired position on the scalp once put in place. In some embodiments, biofeedback aspects of ANNA can be used in conjunction with the tape design 150 to further enhance the capability of improved connectivity and placement of the electrodes and ultimately provide more accurate readings that can be used and fed back into ANNA's database.

In some embodiments, a system includes at least one memory and at least one processor of a computer system communicatively coupled to the at least one memory. The at least one processor can be configured to perform a method including methods described above.

According yet to another embodiment of the present disclosure, a computer readable storage medium comprises computer instructions which, responsive to being executed by one or more processors, cause the one or more processors to perform operations as described in the methods or systems above or elsewhere herein.

Figure 16:
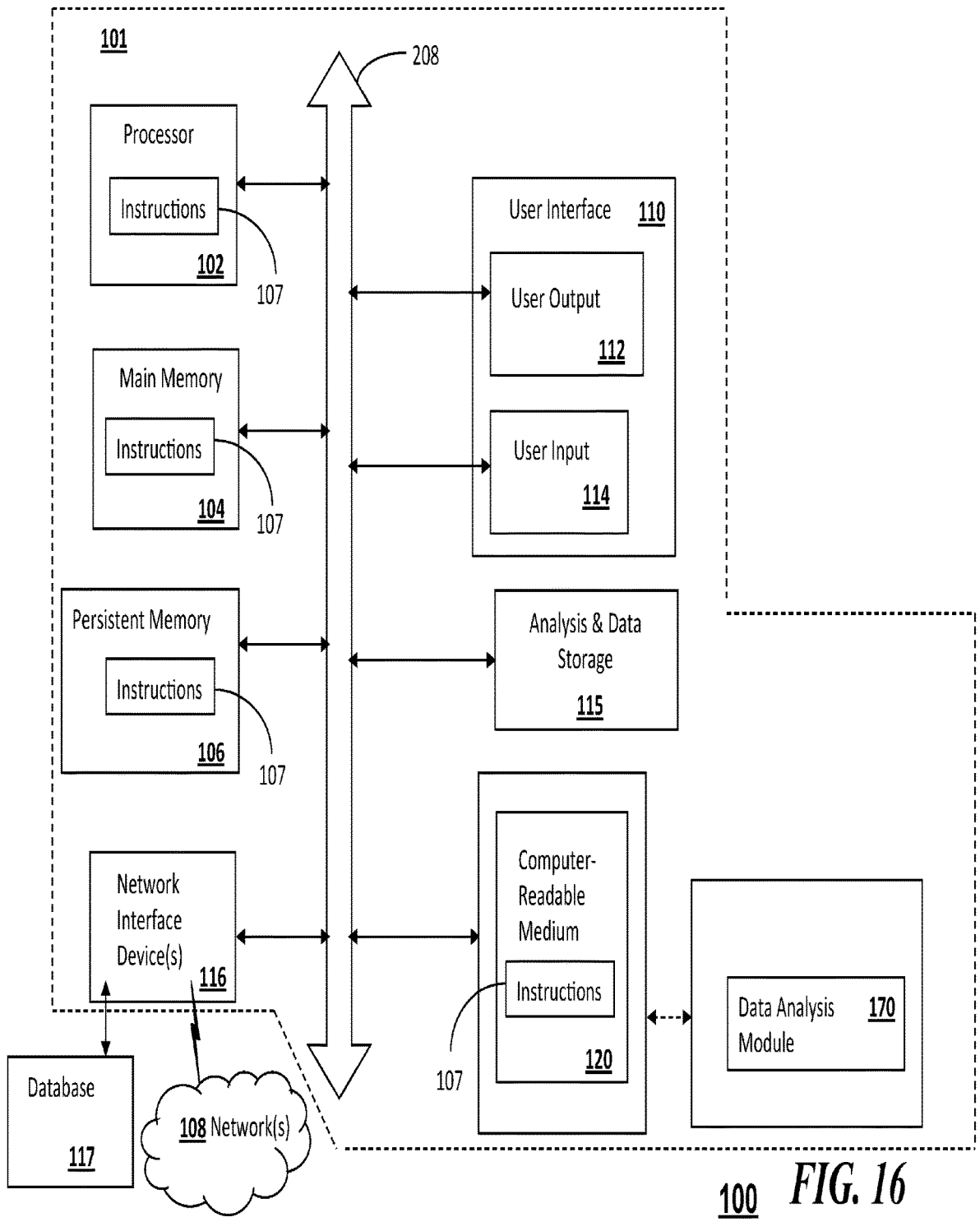
FIG. 16 is a block diagram of a system according to various embodiments of the present disclosure.

As shown in FIG. 16, an information processing system 101 of a system 100 can be communicatively coupled with the data analysis module 170 and a group of client or other devices, or coupled to a presentation device for display at any location at a terminal or server location. According to this example, at least one processor 102, responsive to executing instructions 107, performs operations to communicate with the data analysis module 170 via a bus architecture 208, as shown. The at least one processor 102 is communicatively coupled with main memory 104, persistent memory 106, and a computer readable medium 120. The processor 102 is communicatively coupled with an Analysis & Data Storage 115 that, according to various implementations, can maintain stored information used by, for example, the data analysis module 170 and more generally used by the information processing system 100. Optionally, this stored information can be received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The data analysis module 150170 and the information processing system 100, can use the information from the history log such as in the analysis process and in making decisions related to determining whether data measured is considered an outlier or not.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

In some embodiments, blocks of data are stored in memory subsystems (102, 106, 120, 117, or 108 in cloud based systems) using a blockchain or similar cryptographic hash technology to detect unauthorized modification or corruption of records. Thus, only authorized users such as a patient's physician is able to see the data using a cryptographic key associated with the patient's physician. Moreover, the data can be anonymized so that the identity associated with a subject is anonymous unless the subject gives permission or authorization for this information to be released. In some embodiments, an identifier for one or more blocks in the blockchain includes a private encryption key.

Blockchain technology is widely known as the technology behind the popular cryptocurrency, Bitcoin. A blockchain creates a history of data deposits, messages, or transactions in a series of blocks where each block contains a mathematical summary, called a hash, of the previous block. This creates a chain where any changes made to a block will change that block's hash, which must be recomputed and stored in the next block. This changes the hash of the next block, which must also be recomputed and so on until the end of the chain. The information being transmitted can be encrypted or stored to be only accessible or readable to the user himself or herself, or to someone with appropriate security information. The privacy of the user, or the user's identity, can also be secured and maintained cryptographically. These encryption steps may be performed locally or on a remote device. These encryption steps may be performed on a remote server or on the cloud.

The security of a blockchain is further increased by implementing it on a distributed network. This means a large number of users all have access to the blockchain and are all attempting to add blocks to the end of the chain by finding a nonce that produces a valid hash for a given block of data. When two blocks are found that both claim to reference the same previous block, a fork in the chain is created. Some users in the network will attempt to find the next block on one end of the fork while other users will work from the other end of the fork. Eventually one of the forks will surpass the other in length, and the longest chain is accepted by consensus as the valid chain. Therefore, anyone who attempts to change a block must not only re-find a valid hash for each subsequent block, but must do it faster than everyone else working on the currently accepted chain. Thus, after a certain number of blocks have been chained onto a particular block, it becomes prohibitively costly to try to change that block.

The information processing system 100 includes a user interface 110 that comprises a user output interface 112 and user input interface 114. Examples of elements of the user output interface 112 can include a display, a speaker, one or more indicator lights, one or more transducers that generate audible indicators, and a haptic signal generator. Examples of elements of the user input interface 114 can include a keyboard, a keypad, a mouse, a track pad, a touch pad, a microphone that receives audio signals, a camera, a video camera, or a scanner that scans images. The received audio signals or scanned images, for example, can be converted to electronic digital representation and stored in memory, and optionally can be used with corresponding voice or image recognition software executed by the processor 102 to receive user input data and commands, or to receive test data for example.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can intercommunicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present disclosure. The network interface device 116 can provide a communication interface for the information processing system 100 to access the at least one database 117 according to various embodiments of the disclosure.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

FIGS. 1 and 2 illustrate examples of methods, according to various embodiments of the present disclosure, which can operate in conjunction with the information processing system of FIG. 16.

Figure 18:
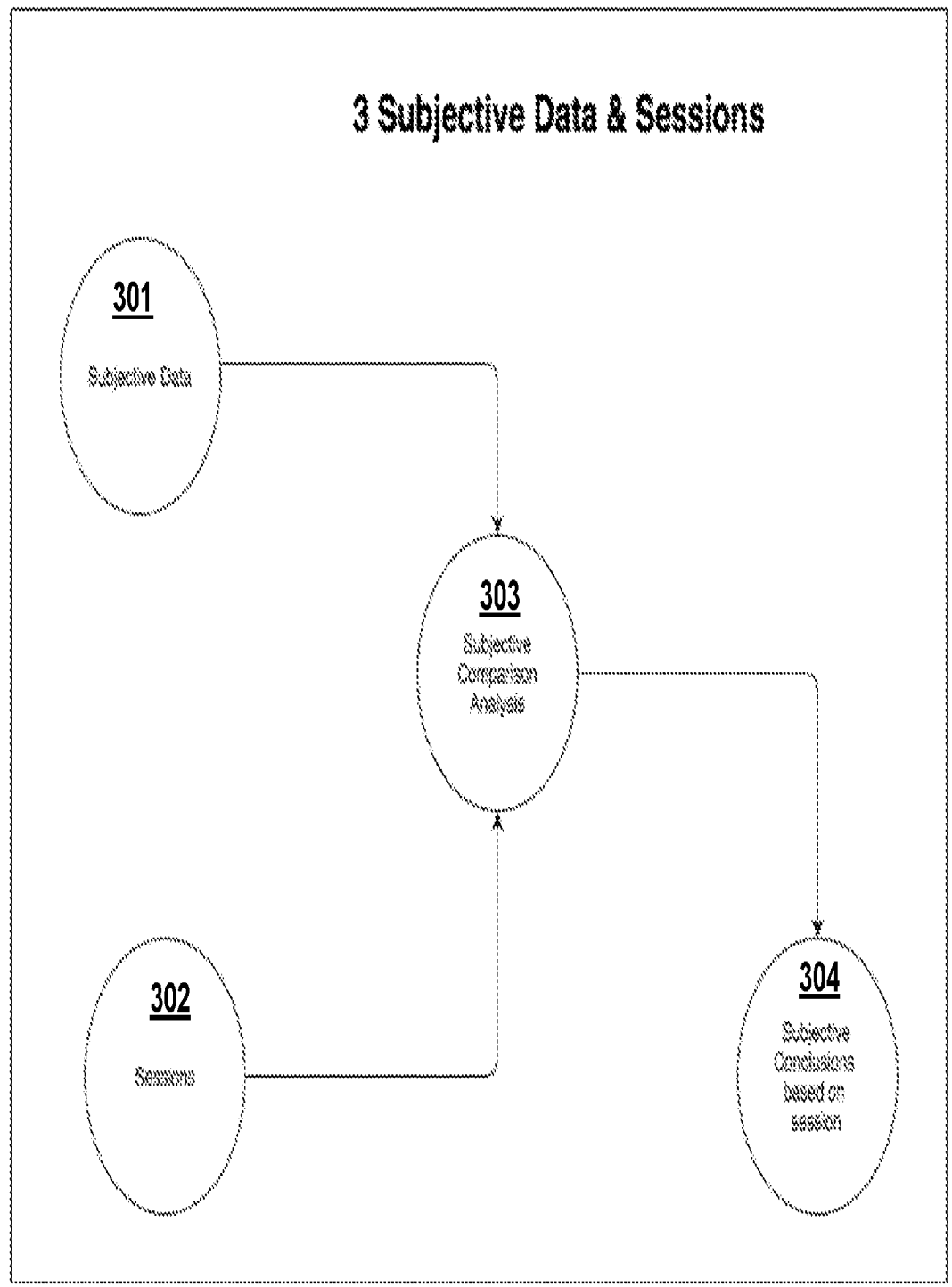

Referring to FIGS. 17A, 17B, and 18, portions or constituent parts of an overall system for ANNA are detail further in block diagrams or flow charts. One overall exemplary block diagram is further illustrated in FIG. 19. With respect to the block diagram 200 of FIG. 17A, a machine learning portion of ANNA can capture raw data in European Data Format (EDF) at block 202 and forward such data for conversion or processing, using, for example, MAT LAB at block 203. MAT LAB formatting and processing will allow easier processing for normalization and conversion to power and connectivity data at block 204. Subsequently, the power and connectivity data can be clustered as desired at block 205. In one example, the clustering can be done over predetermined frequency bands known to provide insights into certain brain-related conditions. With further respect to FIG. 17B, block diagram 201 illustrates a portion of ANNA that can perform subjective rules processing by processing or analyzing at block 207 the power and connectivity data 204 along with subjective rules from a block 206 to provide subjective conclusions at block 208. Some of the subjective rules could be applied as part of a professional's assessment of a patient's condition at the time of the EDF data readings from the patient. For example, if the patient was inattentive, sleepy, fidgety, or in some other subjectively noticeable state, a subjective conclusion can be extracted as part of the process. In some embodiments, the Subjective Rules can be based on a visual or audio recording or assessment without the use of a live professional assessment. In either case, ANNA can be configured to subsequently allow for corrective assessments as previously discussed in another phase of the system.

FIG. 18 illustrates another block diagram 300 depicting a portion of ANNA's system dealing with subjective data and sessions. Block 303 collects and performs a subjective comparison analysis of subjective data from block 301 and from sessions 302. Subjective data can include a patient's self assessments about moods or feelings or other previous assessments and analyzed data can further include data from interactive sessions that probes the patient further regarding their condition. As a result of the subjective comparison analysis 303, the system provides subjective conclusions based on the sessions at block 304.

Figure 19:
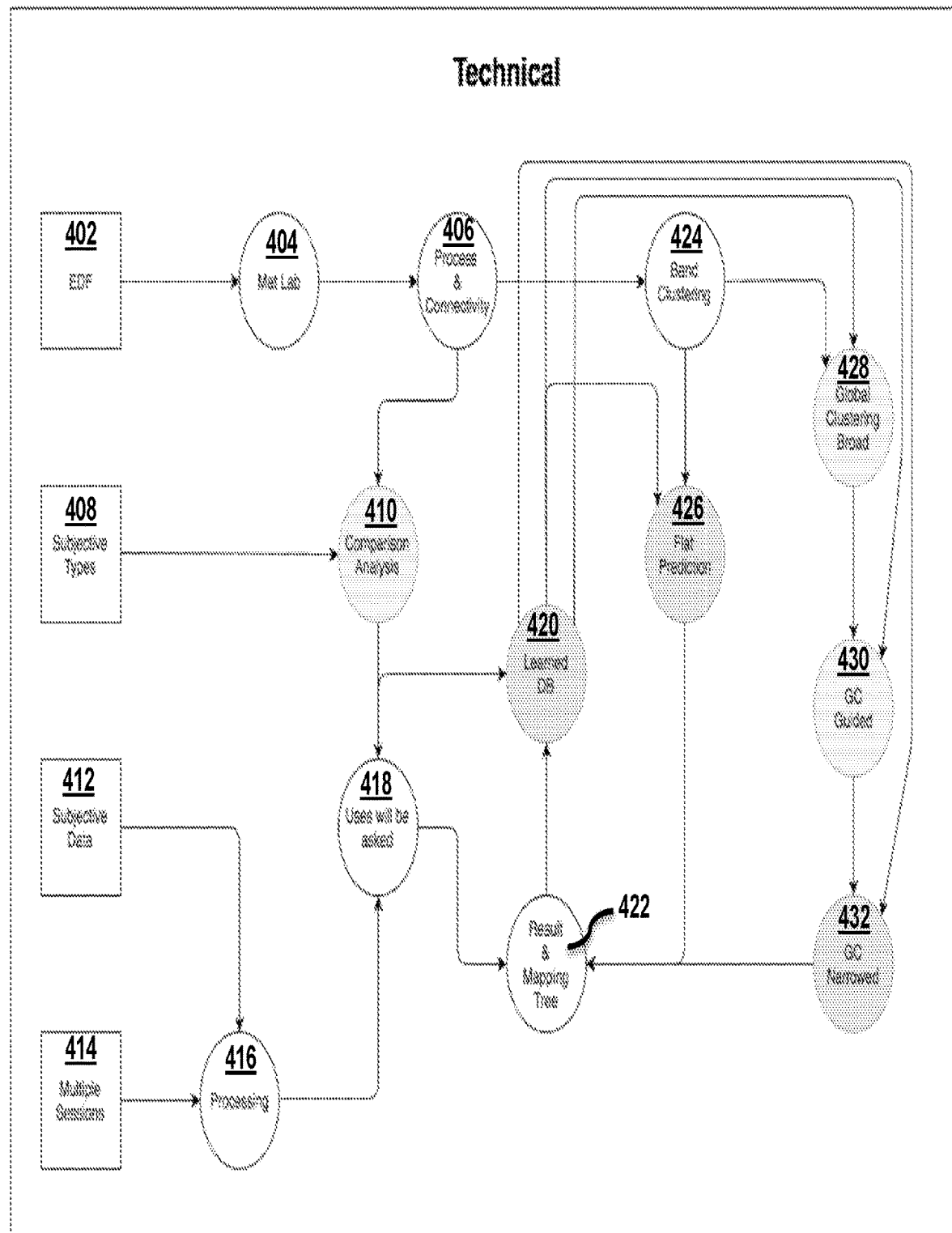
FIG. 19 is a block diagram of a system according to various embodiments of the present disclosure.

FIG. 19 illustrates a block diagram of a system 400 that incorporates a number of the previously disclosed system portions into an overall system in accordance with an embodiment of the disclosure. In this embodiment, raw EDF data from block 402 provides data for conversion or processing into MAT LAB format at block 404 which is further normalized or processed for connectivity at block 406 to further enable comparison analysis at block 410 with subjective type data from block 408. Block 416 collects and performs a subjective comparison analysis of subjective data from block 412 and from sessions 414. As a result of the subjective comparison analysis or other processing at block 416 and the comparison analysis of block 410, the system provides results to block 418 where users or experts will be asked to provide verification and/or corrective actions. The output of block 418 will be further used for building and modifying a mapping tree of symptoms and results. Additionally, ANNA includes a learned database 420 that receives inputs from the comparison analysis block 410 and result and mapping tree block 422.

The learned database 420 provides inputs to all or some of the alternative clustering methods that can be used as part of the overall system to provide predictions of symptoms as a result of clustering (using broad prediction analysis at block 428, or guided prediction analysis at block 430, or narrowed prediction analysis at block 432) or as a result of flat prediction analysis at block 426. Furthermore, the system can incorporate a feedback system that provides the results from any of the prediction analysis techniques (426, 428, 430, or 432) back to the result and mapping tree block 422 for continual refinement and improvement. The blocks 428, 430, and 432 can used global clustering as part of their analysis to cluster results and enable a modified result based on clustering and comparison of data already stored (regarding possible symptoms or other pertinent data) in a database such as the ANNA database or learned database 420. Further note that the system can also cluster gathered patient data over different frequency bands at block 424 before further prediction analysis using clustering techniques at blocks 428, 430 or 430 or without additional clustering with a flat prediction at block 426. As an integrated system, system 400 can use machine learning, artificial intelligence and other techniques to continually improve and provide the next generation of psychiatric analysis and medicine as a tool for clinics, hospitals, individual licensed practitioners, and other users with appropriate guidance and instruction or supervision.

Figure 20:
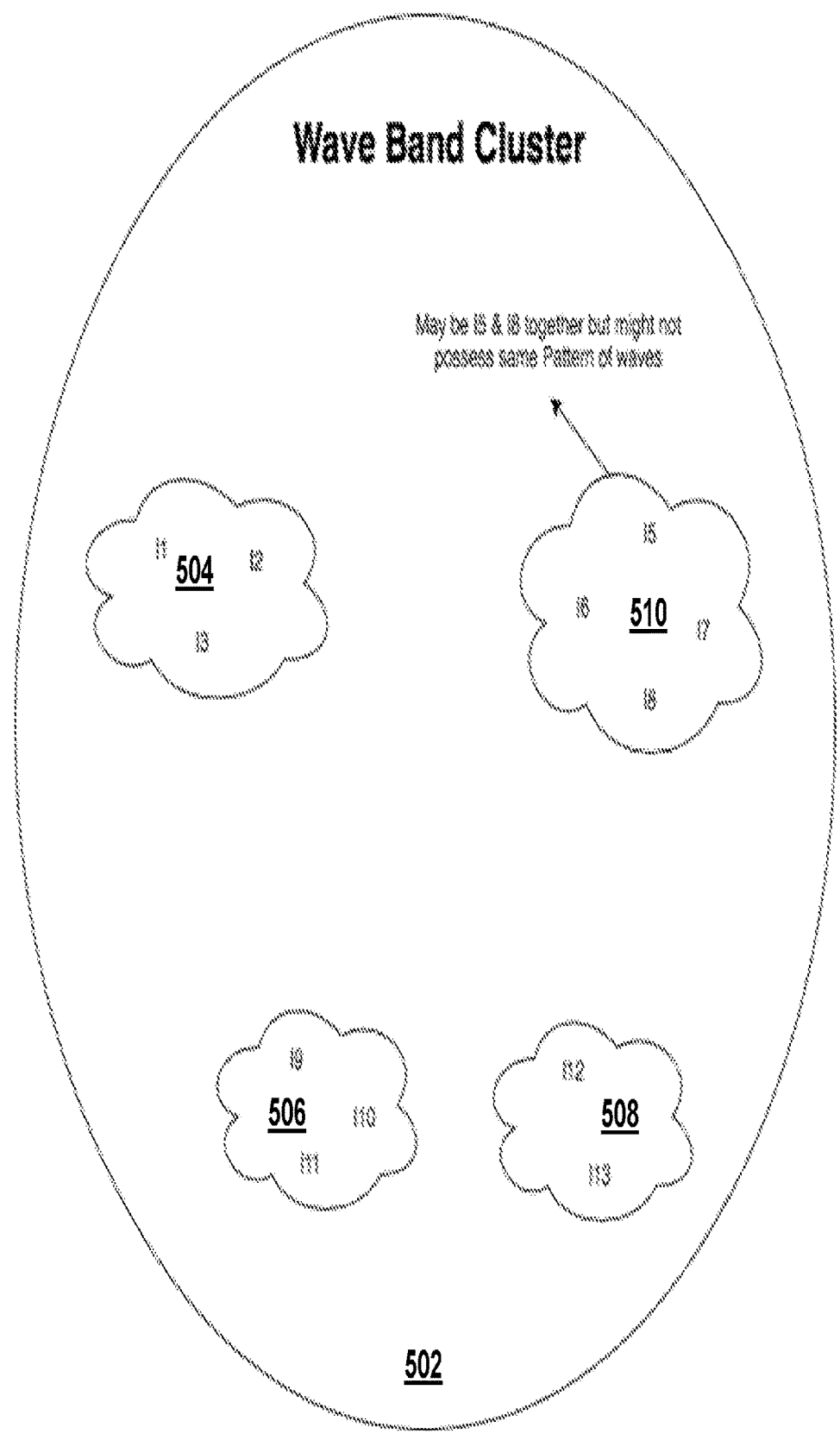
FIG. 20 is an illustration of a wave band cluster in accordance with various embodiments of the present disclosure.

FIG. 20 illustrates a wave band cluster 502 for a system 500 having various clusters 504, 506, 508, and 510. Each of these clusters might represent clusters for particular frequency bands (e.g., Gamma, Beta, Low Beta, Midrange Beta, High Beta, Alpha, etc.) for EEG signals captured at particular sites on the skull or correlated with particular locations of the brain (frontal lobes, occipital lobes, temporal lobes, central strip, parietal lobes, etc.). These clustered signals can provide some predictive indications, but further clustering of these various clusters (504-510) during global clustering can also provide additional predictive indications of symptoms as discussed above.

Non-Limiting Examples

The examples provide herein may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present specification may describe components and functions implemented in the embodiments with reference to particular standards and protocols, the disclosure is not limited to such standards and protocols. Each of the standards represents examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single example embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Although only one processor is illustrated for an information processing system, information processing systems with multiple CPUs or processors can be used equally effectively. Various embodiments of the present disclosure can further incorporate interfaces that each includes separate, fully programmed microprocessors that are used to off-load processing from the processor. An operating system (not shown) included in main memory for the information processing system may be a suitable multitasking and/or multiprocessing operating system, such as, but not limited to, any of the Linux, UNIX, Windows, and Windows Server based operating systems. Various embodiments of the present disclosure are able to use any other suitable operating system. Various embodiments of the present disclosure utilize architectures, such as an object oriented framework mechanism, that allows instructions of the components of operating system (not shown) to be executed on any processor located within the information processing system. Various embodiments of the present disclosure are able to be adapted to work with any data communications connections including present day analog and/or digital techniques or via a future networking mechanism.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The terms "communicatively coupled" or "communicatively coupling" include, but are not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The terms "controller", "computer", "processor", "server", "client", "computer system", "computing system", "personal computing system", "processing system", or "information processing system", describe examples of a suitably configured processing system adapted to implement one or more embodiments herein. Any suitably configured processing system is similarly able to be used by embodiments herein, for example and not for limitation, a personal computer, a laptop personal computer (laptop PC), a tablet computer, a smart phone, a mobile phone, a wireless communication device, a personal digital assistant, a workstation, and the like. A processing system may include one or more processing systems or processors. A processing system can be realized in a centralized fashion in one processing system or in a distributed fashion where different elements are spread across several interconnected processing systems.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. A computer implemented method of analyzing electroencephalogram signals, comprising:
    capturing the electroencephalogram signals using a plurality of sensors contacting a skull;
    clustering, by one or more processors, the electroencephalogram signals using at least stored objective data and subjective data including patient profile data to provide clustered data results; and
    predicting, by the one or more processors, a diagnosis based on the clustered data results,
    wherein the one or more processors present options for predicting the diagnosis using a selection among an unguided prediction, a guided prediction, a narrowed down prediction, or a flat prediction.

2. The method of claim 1, wherein the one or more processors are configured to perform data transformation of the electroencephalogram signals to enable a comparison of normalized electroencephalogram signals with the stored objective data.

3. The method of claim 2, wherein the data transformation is done by using one or more of the analysis methods comprising absolute power analysis, relative power analysis, amplitude asymmetry connectivity analysis, coherence connectivity analysis, phase lag analysis, phase shift analysis, phase lock analysis or source density vector averaging.

4. The method of claim 1, wherein the one or more processors clusters the electroencephalogram signals using a K-Means algorithm.

5. The method of claim 1, wherein the one or more processors, in response to predicting a diagnosis based on the clustered data results, presents an option enabling an expert to correct or verify the diagnosis predicted by the method.

* * * * *